United States Patent
Shanmugam et al.

(10) Patent No.: US 12,357,629 B2
(45) Date of Patent: Jul. 15, 2025

(54) USES OF BCL-2 ANTAGONISTS FOR TREATING CANCER AND DIAGNOSTICS RELATED THERETO

(71) Applicant: Emory University, Atlanta, GA (US)

(72) Inventors: Malathy Shanmugam, Atlanta, GA (US); Richa Bajpai, Decatur, GA (US)

(73) Assignee: Emory University, Atlanta, GA (US)

( * ) Notice: Subject to any disclaimer, the term of this patent is extended or adjusted under 35 U.S.C. 154(b) by 701 days.

(21) Appl. No.: 17/676,666

(22) Filed: Feb. 21, 2022

(65) Prior Publication Data

US 2022/0175767 A1 Jun. 9, 2022

Related U.S. Application Data

(62) Division of application No. 16/396,012, filed on Apr. 26, 2019, now abandoned.

(60) Provisional application No. 62/663,104, filed on Apr. 26, 2018.

(51) Int. Cl.
| | | |
|---|---|---|
| *A61K 31/496* | (2006.01) | |
| *A61K 31/381* | (2006.01) | |
| *A61K 31/44* | (2006.01) | |
| *A61P 35/02* | (2006.01) | |
| *A61K 45/06* | (2006.01) | |

(52) U.S. Cl.
CPC .......... *A61K 31/496* (2013.01); *A61K 31/381* (2013.01); *A61K 31/44* (2013.01); *A61P 35/02* (2018.01); *A61K 45/06* (2013.01)

(58) Field of Classification Search
CPC ...... A61K 31/496; A61K 31/381; A61P 35/02
USPC .................................................. 514/252.12
See application file for complete search history.

(56) References Cited

U.S. PATENT DOCUMENTS

| | | | |
|---|---|---|---|
| 9,345,702 B2 | 5/2016 | Elmore | |
| 2016/0113925 A1 | 4/2016 | Shanmugam | |

FOREIGN PATENT DOCUMENTS

| | | |
|---|---|---|
| WO | 2005049593 | 6/2005 |
| WO | 2016024230 | 2/2016 |
| WO | 2017079399 | 5/2017 |

OTHER PUBLICATIONS

Guo et al Journal of Biological Chemistry, 2016, 291(1), 42-57 (Year: 2016).*

Bajpai et al. Targeting glutamine metabolism in multiple myeloma enhances BIM binding to BCL-2 eliciting synthetic lethality to venetoclax, Oncogene (2016) 35, 3955-3964.
Bajpai et al. Succinate Ubiquinone Reductase Activity Predicts Multiple Myeloma Sensitivity to Venetoclax, Abstract, 652. Myeloma: Pathophysiology and Pre-Clinical Studies, excluding Therapy: Poster Dec. 7, 2017.
Bajpai et al. Glutamine deprivationelicited sensitization of multiple myeloma to venetoclax is associated with electron transport chain inhibition, Abstract 2028A: Proceedings: AACR Annual Meeting 2017, Jul. 2017.
Bajpai et al. Glutamine deprivationelicited sensitization of multiple myeloma to venetoclax is associated with electron transport chain inhibition, Proceedings: AACR Annual Meeting 2017 AACR, Poster Apr. 1-5, 2017.
Bajpai et al.Targeting cancer metabolism through synthetic lethality-based combinatorial treatment strategies, Oncology, 2018, 30(5), 338.
Bajpai et al. Electron transport chain activity is a predictor and target for venetoclax sensitivity in multiple myeloma, Nat Commun, 2020, 11(1):1228.
Commander et al. Subpopulation targeting of pyruvate dehydrogenase and GLUT1 decouples metabolic heterogeneity during collective cancer cell invasion, Nat Commun. 2020, 11(1):1533.
Kruspig et al. Targeting succinate:ubiquinone reductase potentiates the efficacy of anticancer therapy, Biochimica et Biophysica Acta 1863 (2016) 2065-2071.
Leiba et al. Translocation t(11;14) in Newly Diagnosed Patients with Multiple Myeloma: Is It Always Favorable? Genes, Chromosomes & Cancer 55:710-718 (2016).
Pollyea et al. Venetoclax with Azacitidine Disrupts Energy Metabolism and Targets Leukemia Stem Cells in Acute Myeloid Leukemia Patients, Nat Med, 2018, 24(12): 1859-1866.
Shanmagam et al. Glutamine Deprivation-elicitedSensitization of Multiple Myeloma toVenetoclax is Associated With Electron Transport Chain Inhibition, 16th International Myeloma Workshop, 2017, Abstract, OP-020.
Wang et al. Synthesis and Antineoplastic Evaluation of Mitochondrial Complex II (Succinate Dehydrogenase) Inhibitors Derived from Atpenin A5, ChemMedChem 2017, 12, 1033-1044.
Wei et al., Development of GLUT4-selective antagonists for multiple myeloma therapy, Nat Commun, 2020, 11(1):1533.
Wei et al., Glutamine Catabolismaintains MCL-1 Expression in Glucose-Deprived Multiple Myeloma, Blood (2017) 130 (Supplement 1): 3076.
McBrayer et al. Multiple myeloma exhibits novel dependence on GLUT4, GLUT8, and GLUT11: implications for glucose transporter-directed therapy, Blood, 2012, vol. 119, No. 20, 4686.

* cited by examiner

*Primary Examiner* — Yevgeny Valenrod
(74) *Attorney, Agent, or Firm* — Emory Patent Group

(57) ABSTRACT

In certain embodiments, this disclosure relates to method of treating and diagnosing cancer by administering a Bcl-2 inhibitor optionally in combination with a mitochondrial complex II inhibitor. In certain embodiments, a subject is diagnosed with, exhibiting symptoms of, or at risk of cancer wherein the cancer is a hematological malignancy such as multiple myeloma, leukemia, or lymphoma.

9 Claims, 5 Drawing Sheets

USES OF BCL-2 ANTAGONISTS FOR TREATING CANCER AND DIAGNOSTICS RELATED THERETO

CROSS-REFERENCE TO RELATED APPLICATIONS

This application is a division of U.S. application Ser. No. 16/396,012 filed Apr. 26, 2019, which claims the benefit of U.S. Provisional Application No. 62/663,104 filed Apr. 26, 2018. The entirety of each of these applications is hereby incorporated by reference for all purposes.

STATEMENT REGARDING FEDERALLY SPONSORED RESEARCH OR DEVELOPMENT

This invention was made with government support under CA208328 awarded by the National Institutes of Health. The government has certain rights in the invention.

BACKGROUND

Overexpression of the Bcl-2 family members is commonly associated with tumor maintenance, progression, and chemoresistance. Inhibitors of Bcl-2 family members promote apoptosis of cancer cells. Venetoclax (VENCLEXTA™) is a Bcl-2 antagonist used to treat chronic lymphocytic leukemia (CLL). Elmore et al. report methods of treatment using selective Bcl-2 inhibitors. U.S. Pat. No. 9,345,702. See also WO 2005/049593, and WO 2005/024636.

Multiple myeloma (MM) is a plasma cell malignancy. The development of chemo-resistant MM is common, with approximately 20% of patients succumbing to aggressive treatment-refractory disease within a short period of diagnosis. Resistance is primarily associated with evasion of apoptosis connected to the inability to release sufficient pro-apoptotic Bcl-2 proteins. Thus, finding improved therapeutic strategies are needed.

A common translocation in multiple myeloma (MM) is t(11;14)(q13;q32). According to several studies, this translocation represents a unique subset of patients with worse than standard risk outcomes. Certain chromosomal aberrations in combination with t(11;14) alone are also reported. See Leiba et al. Genes Chromosomes Cancer. 2016, 55(9): 710-8. About 40% of the t(11;14) exhibiting patients are responsive to single agent venetoclax. Thus, there is a need to find improved diagnostic strategies.

Bajpai et al. report targeting glutamine metabolism in multiple myeloma enhances BIM binding to Bcl-2 eliciting synthetic lethality to venetoclax. Oncogene, 2016, 35(30): 3955-64.

References cited herein are not an admission of prior art.

SUMMARY

In certain embodiments, this disclosure relates to method of treating and diagnosing cancer by administering a Bcl-2 inhibitor optionally in combination with a mitochondrial complex II inhibitor. In certain embodiments, a subject is diagnosed with, exhibiting symptoms of, or at risk of cancer wherein the cancer is a hematological malignancy such as multiple myeloma, leukemia, or lymphoma.

In certain embodiments, this disclosure relates to methods of treating cancer comprising administering an effective amount of a Bcl-2 inhibitor in combination with a mitochondrial complex II inhibitor to a subject in need thereof. In certain embodiments, the mitochondrial complex II inhibitor is thenoyltrifluoroacetone or atpenin A5. In certain embodiments, the Bcl-2 inhibitor is venetoclax or navitoclax or derivative thereof.

In certain embodiments, this disclosure relates to a method of treating multiple myeloma comprising administering an effective amount of venetoclax in combination with a thenoyltrifluoroacetone or atpenin A5 to a subject in need thereof.

In certain embodiments, the subject is diagnosed with cancer or hematological malignancy. In certain embodiments, the hematological malignancy is multiple myeloma, leukemia, or lymphoma. In certain embodiments, the hematological malignancy is acute lymphoblastic leukemia (ALL), acute myelogenous leukemia (AML), chronic lymphocytic leukemia (CLL), small lymphocytic lymphoma (SLL), chronic myelogenous leukemia, acute monocytic leukemia (AMOL), Hodgkin's lymphomas, and non-Hodgkin's lymphomas such as Burkitt lymphoma, B-cell lymphoma.

In certain embodiments, this disclosure contemplates identifying t(11;14) patients who will respond to venetoclax as well to identifying strategies to sensitize the broader resistant (t(11;14) and non t(11;14) myeloma population to venetoclax.

In certain embodiments, this disclosure relates to methods comprising, a) isolating a sample of cancer cells from a subject, b) mixing the sample with mitochondrial complex II, succinate, and ubiquinone; and c) measuring succinate ubiquinone reductase (SQR) activity providing measured SQR activity. In certain embodiments, the method further comprises diagnosing the subject as sensitive to or in need of a chemotherapy treatment comprising administering a Bcl-2 inhibitor in combination with a mitochondrial complex II inhibitor, if the measured SQR activity is higher than a control level. In certain embodiments, the subject is or is not diagnosed with a t(11;14) translocation.

In certain embodiments, the method further comprises diagnosing the subject as not in need of or would not benefit from a chemotherapy comprising administering Bcl-2 inhibitor in combination with a mitochondrial complex II inhibitor, if the measured SQR activity is lower than a control level.

In certain embodiments, the method further comprises the step of recording the measurements. In certain embodiments, the measurements are recorded in an electronic format. In certain embodiments, the method further comprises the step of recording the diagnosis. In certain embodiments, the diagnosis is recorded in an electronic format. In certain embodiments, the method further comprises the step of reporting the measurements or diagnosis to a medical professional, the subject, or representative thereof. In certain embodiments, the method further comprises administering an effective amount of a combination therapy of Bcl-2 inhibitor in combination with a mitochondrial complex II inhibitor to the subject.

In certain embodiments, this disclosure relates to methods of diagnosing and treating multiple myeloma comprising, a) isolating a sample of myeloma cells from a subject, b) mixing the sample with mitochondrial complex II, succinate, and ubiquinone; and c) measuring succinate ubiquinone reductase (SQR) activity providing measured SQR activity; and d) treating the subject with a Bcl-2 inhibitor in combination with mitochondrial complex II inhibitor if the measured SQR activity is higher than a control level.

In certain embodiments, this disclosure relates to methods of diagnosing and treating multiple myeloma comprising, a) isolating a sample of myeloma cells from a subject, b) mixing the sample with mitochondrial complex II, succinate, and ubiquinone; and c) measuring succinate ubiquinone reductase (SQR) activity providing measured SQR activity; and d) treating the subject with venetoclax in combination with thenoyltrifluoroacetone or atpenin A5 if the measured SQR activity is higher than a control level.

In certain embodiments, administering an effective amount of a Bcl-2 inhibitor in combination with a mitochondrial complex II inhibitor is further in combination with an additional chemotherapy agent. In certain embodiments, an additional chemotherapy agent or combination is contemplated to be selected from abemaciclib, abiraterone acetate, methotrexate, paclitaxel, adriamycin, acalabrutinib, brentuximab vedotin, ado-trastuzumab emtansine, aflibercept, afatinib, netupitant, palonosetron, imiquimod, aldesleukin, alectinib, alemtuzumab, pemetrexed disodium, copanlisib, melphalan, brigatinib, chlorambucil, amifostine, aminolevulinic acid, anastrozole, apalutamide, aprepitant, pamidronate disodium, exemestane, nelarabine, arsenic trioxide, ofatumumab, atezolizumab, bevacizumab, avelumab, axicabtagene ciloleucel, axitinib, azacitidine, carmustine, belinostat, bendamustine, inotuzumab ozogamicin, bevacizumab, bexarotene, bicalutamide, bleomycin, blinatumomab, bortezomib, bosutinib, brentuximab vedotin, brigatinib, busulfan, irinotecan, capecitabine, fluorouracil, carboplatin, carfilzomib, ceritinib, daunorubicin, cetuximab, cisplatin, cladribine, cyclophosphamide, clofarabine, cobimetinib, cabozantinib-S-malate, dactinomycin, crizotinib, ifosfamide, ramucirumab, cytarabine, dabrafenib, dacarbazine, decitabine, daratumumab, dasatinib, defibrotide, degarelix, denileukin diftitox, denosumab, dexamethasone, dexrazoxane, dinutuximab, docetaxel, doxorubicin, durvalumab, rasburicase, epirubicin, elotuzumab, oxaliplatin, eltrombopag olamine, enasidenib, enzalutamide, eribulin, vismodegib, erlotinib, etoposide, everolimus, raloxifene, toremifene, panobinostat, fulvestrant, letrozole, filgrastim, fludarabine, flutamide, pralatrexate, obinutuzumab, gefitinib, gemcitabine, gemtuzumab ozogamicin, glucarpidase, goserelin, propranolol, trastuzumab, topotecan, palbociclib, ibritumomab tiuxetan, ibrutinib, ponatinib, idarubicin, idelalisib, imatinib, talimogene laherparepvec, ipilimumab, romidepsin, ixabepilone, ixazomib, ruxolitinib, cabazitaxel, palifermin, pembrolizumab, ribociclib, tisagenlecleucel, lanreotide, lapatinib, olaratumab, lenalidomide, lenvatinib, leucovorin, leuprolide, lomustine, trifluridine, olaparib, vincristine, procarbazine, mechlorethamine, megestrol, trametinib, temozolomide, methylnaltrexone bromide, midostaurin, mitomycin C, mitoxantrone, plerixafor, vinorelbine, necitumumab, neratinib, sorafenib, nilutamide, nilotinib, niraparib, nivolumab, tamoxifen, romiplostim, sonidegib, omacetaxine, pegaspargase, ondansetron, osimertinib, panitumumab, pazopanib, interferon alfa-2b, pertuzumab, pomalidomide, mercaptopurine, regorafenib, rituximab, rolapitant, rucaparib, siltuximab, sunitinib, thioguanine, temsirolimus, thalidomide, thiotepa, trabectedin, valrubicin, vandetanib, vinblastine, vemurafenib, vorinostat, zoledronic acid, or combinations thereof.

DETAILED DESCRIPTION

Figure 1A:
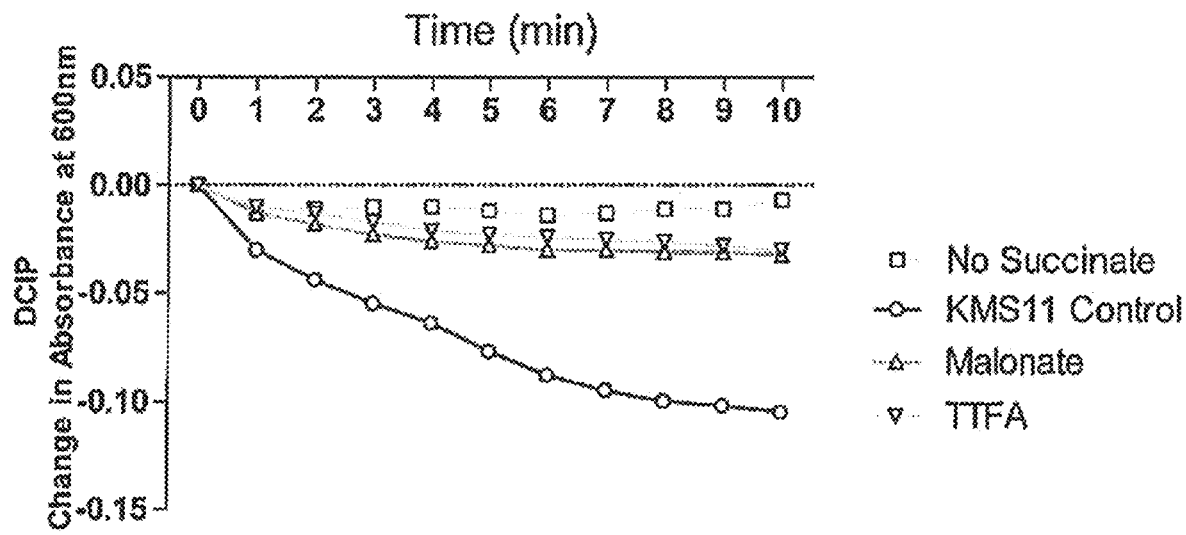
FIG. 1A shows data of the SQR activity assay in KMS11 cells. Cells are resuspended in permeabilization buffer (10 mM $KH_2PO_4$ pH 7.8, 2 mM EDTA and 1 mg/ml BSA). 20 mM succinate is added as a substrate with or without 5 mM malonate (an SDH inhibitor) followed by a 10 min incubation at RT. SQR activity is determined by measuring electron transfer from succinate to decylubiquinone and 2,6-dichlorophenolindophenol (DCPIP) that leads to a change in absorbance of DCPIP monitored at 600 nm for 10 min.

Before the present disclosure is described in greater detail, it is to be understood that this disclosure is not limited to particular embodiments described, and as such may, of course, vary. It is also to be understood that the terminology used herein is for the purpose of describing particular embodiments only, and is not intended to be limiting, since the scope of the present disclosure will be limited only by the appended claims.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present disclosure is not entitled to antedate such publication by virtue of prior disclosure.

Further, the dates of publication provided could be different from the actual publication dates that may need to be independently confirmed.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically possible.

Embodiments of the present disclosure will employ, unless otherwise indicated, techniques of immunology, medicine, organic chemistry, biochemistry, molecular biology, pharmacology, physiology, and the like, which are within the skill of the art. Such techniques are explained fully in the literature.

It must be noted that, as used in the specification and the appended claims, the singular forms "a," "an," and "the" include plural referents unless the context clearly dictates otherwise. In this specification and in the claims that follow, reference will be made to a number of terms that shall be defined to have the following meanings unless a contrary intention is apparent.

Prior to describing the various embodiments, the following definitions are provided and should be used unless otherwise indicated.

To the extent that structures provided herein are compounds with tautomers by hydrogen migration, a skilled artisan would understand the formula to cover all tautomeric forms.

As used herein, "salts" refer to derivatives of the disclosed compounds where the parent compound is modified making acid or base salts thereof. Examples of salts include, but are not limited to, mineral or organic acid salts of basic residues such as amines, alkylamines, or dialkylamines; alkali or organic salts of acidic residues such as carboxylic acids; and the like. In preferred embodiment, the salts are conventional nontoxic pharmaceutically acceptable salts including the quaternary ammonium salts of the parent compound formed, and non-toxic inorganic or organic acids. Preferred salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and the like.

"Subject" refers any animal, preferably a human patient, livestock, or domestic pet.

As used herein, the terms "prevent" and "preventing" include the prevention of the recurrence, spread or onset. It is not intended that the present disclosure be limited to complete prevention. In some embodiments, the onset is delayed, or the severity of the disease is reduced.

As used herein, the terms "treat" and "treating" are not limited to the case where the subject (e.g. patient) is cured and the disease is eradicated. Rather, embodiments, of the present disclosure also contemplate treatment that merely reduces symptoms, and/or delays disease progression.

"Cancer" refers any of various cellular diseases with malignant neoplasms characterized by the proliferation of cells. It is not intended that the diseased cells must actually invade surrounding tissue and metastasize to new body sites. Cancer can involve any tissue of the body and have many different forms in each body area. Within the context of certain embodiments, whether "cancer is reduced" may be identified by a variety of diagnostic manners known to one skill in the art including, but not limited to, observation the reduction in size or number of tumor masses or if an increase of apoptosis of cancer cells observed, e.g., if more than a 5% increase in apoptosis of cancer cells is observed for a sample compound compared to a control without the compound. It may also be identified by a change in relevant biomarker or gene expression profile, such as PSA for prostate cancer, HER2 for breast cancer, or others.

The term "prodrug" refers to an agent that is converted into a biologically active form in vivo. Prodrugs are often useful because, in some situations, they may be easier to administer than the parent compound. They may, for instance, be bioavailable by oral administration whereas the parent compound is not. The prodrug may also have improved solubility in pharmaceutical compositions over the parent drug. A prodrug may be converted into the parent drug by various mechanisms, including enzymatic processes and metabolic hydrolysis.

As used herein, the term "derivative" refers to a structurally similar compound that retains sufficient functional attributes of the identified analogue. The derivative may be structurally similar because it is lacking one or more atoms, substituted, a salt, in different hydration/oxidation states, or because one or more atoms within the molecule are switched, such as, but not limited to, replacing an oxygen atom with a sulfur or nitrogen atom or replacing an amino group with a hydroxyl group or vice versa. The derivative may be a prodrug. Derivatives may be prepare by any variety of synthetic methods or appropriate adaptations presented in synthetic or organic chemistry text books, such as those provide in March's Advanced Organic Chemistry: Reactions, Mechanisms, and Structure, Wiley, 6th Edition (2007) Michael B. Smith or Domino Reactions in Organic Synthesis, Wiley (2006) Lutz F. Tietze hereby incorporated by reference.

The term "substituted" refers to a molecule wherein at least one hydrogen atom is replaced with a substituent. When substituted, one or more of the groups are "substituents" or "radicals." The molecule may be multiply substituted. In the case of an oxo substituent ("=O"), two hydrogen atoms are replaced. Example substituents within this context may include halogen, hydroxy, alkyl, alkoxy, nitro, cyano, oxo, carbocyclyl, carbocycloalkyl, heterocarbocyclyl, heterocarbocycloalkyl, aryl, arylalkyl, heteroaryl, heteroarylalkyl, —NRaRb, —NRaC(=O)Rb, —NRaC(=O)NRaNRb, —NRaC(=O)ORb, —NRaSO2Rb, —C(=O)Ra, —C(=O)ORa, —C(=O)NRaRb, —OC(=O)NRaRb, —ORa, —SRa, —SORa, —S(=O)2Ra, —OS(=O)2Ra and —S(=O)2ORa. Ra and Rb in this context may be the same or different and independently hydrogen, halogen hydroxyl, alkyl, alkoxy, alkyl, amino, alkylamino, dialkylamino, carbocyclyl, carbocycloalkyl, heterocarbocyclyl, heterocarbocycloalkyl, aryl, arylalkyl, heteroaryl, and heteroarylalkyl.

If a substituent is described as being "substituted", a non-hydrogen radical is in the place of hydrogen radical on a carbon or nitrogen of the substituent. Thus, for example, a substituted alkyl substituent is an alkyl substituent in which at least one non-hydrogen radical is in the place of a hydrogen radical on the alkyl substituent. To illustrate, monofluoroalkyl is alkyl substituted with a fluoro radical, and difluoroalkyl is alkyl substituted with two fluoro radicals. It should be recognized that if there are more than one substitution on a substituent, each non-hydrogen radical may be identical or different (unless otherwise stated).

If a substituent is described as being "optionally substituted", the substituent may be either (1) not substituted or (2) substituted. If a substituent is described as being optionally substituted with up to a particular number of non-hydrogen radicals, that substituent may be either (1) not substituted; or (2) substituted by up to that particular number of non-hydrogen radicals or by up to the maximum number of substitutable positions on the substituent, whichever is less. Thus, for example, if a substituent is described as a heteroaryl optionally substituted with up to 3 non-hydrogen radicals, then any heteroaryl with less than 3 substitutable positions would be optionally substituted by up to only as many non-hydrogen radicals as the heteroaryl has substitutable positions. To illustrate, tetrazolyl (which has only one substitutable position) would be optionally substituted with up to one non-hydrogen radical. To illustrate further, if an amino nitrogen is described as being optionally substituted with up to 2 non-hydrogen radicals, then a primary amino nitrogen will be optionally substituted with up to 2 non-hydrogen radicals, whereas a secondary amino nitrogen will be optionally substituted with up to only 1 non-hydrogen radical.

As used herein, "mitochondrial complex II" refers to succinate dehydrogenase that is a membrane complex in the Krebs cycle (tricarboxylic acid cycle). Mitochondrial complex II catalyzes the oxidation of succinate to fumarate and transfers the released electrons to ubiquinone, referred to as succinate ubiquinone reductase (SQR) activity. Succinate oxidation is coupled to reduction of ubiquinone to ubiquinol at the mitochondrial inner membrane as one part of the respiration electron transfer chain. Mitochondrial complex II is sometimes referred to as mitochondrial succinate:ubiquinone oxidoreductase (mitochondrial SQR).

"Thenoyltrifluoroacetone" refers to a compound with the chemical name: 4,4,4-trifluoro-1-(thiophen-2-yl)butane-1,3-dione or salts thereof, with the chemical structure below, also referred to as TTFA.

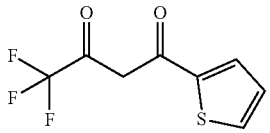 [SMILES: O=C(CC(=O)C(F)(F)F)c1cccs1]

As used herein, "venetoclax" refers to a compound with the chemical name: 4-(4-{[2-(4-chlorophenyl)-4,4-dimethylcyclohex-1-en-1-yl]methyl}piperazin-1-yl)-N-({3-nitro-4-[(tetrahydro-2H-pyran-4-ylmethyl)amino]phenyl} sulfonyl)-2-(1H-pyrrolo[2,3-b]pyridin-5-yloxy)benzamide and salts thereof, with the chemical structure below, also referred to as ABT-199.

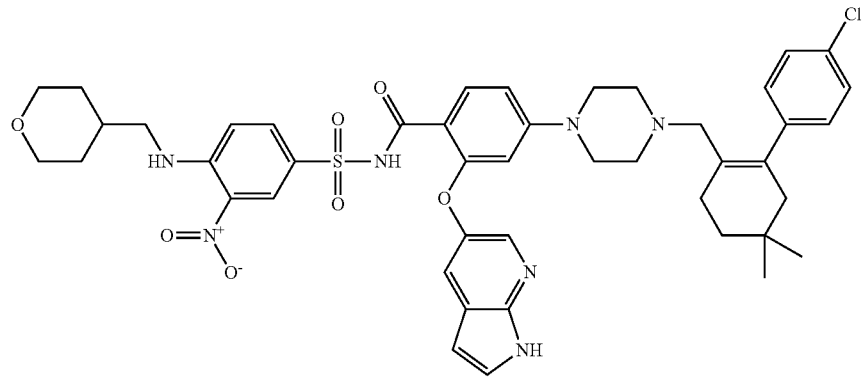 [SMILES: CC1(C)CCC(CN2CCN(c3ccc(C(=O)NS(=O)(=O)c4ccc(NCC5CCOCC5)c([N+](=O)[O-])c4)c(Oc4cnc5[nH]ccc5c4)c3)CC2)=C(c2ccc(Cl)cc2)C1]

In certain embodiments, derivatives of venetoclax include the following compounds:

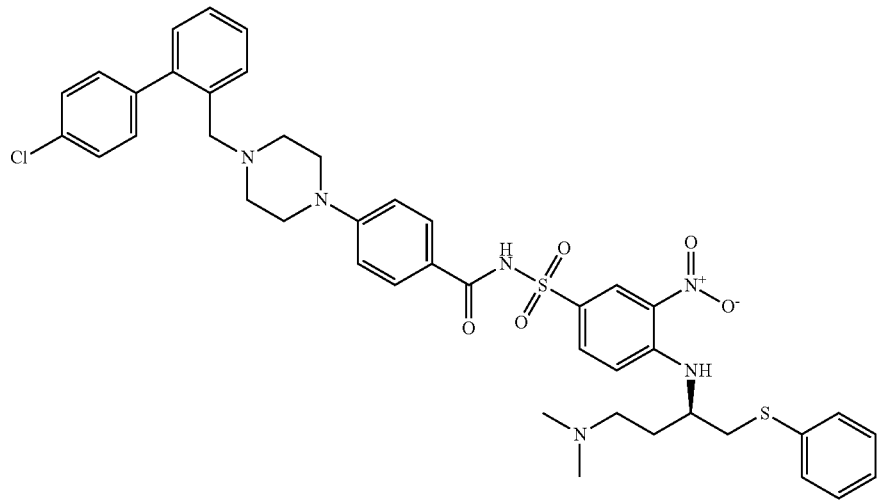 [SMILES: CN(C)CC[C@H](CSc1ccccc1)Nc1ccc(S(=O)(=O)NC(=O)c2ccc(N3CCN(Cc4ccccc4-c4ccc(Cl)cc4)CC3)cc2)cc1[N+](=O)[O-]]

4-[4-[(4'-chloro[1,1'-biphenyl]-2-yl)methyl]-1-piperazinyl]-N-[[4-[[(1R)-3-(dimethylamino)-1-[(phenylthio)methyl]propyl]amino]-3-nitrophenyl]sulfonyl]-benzamide

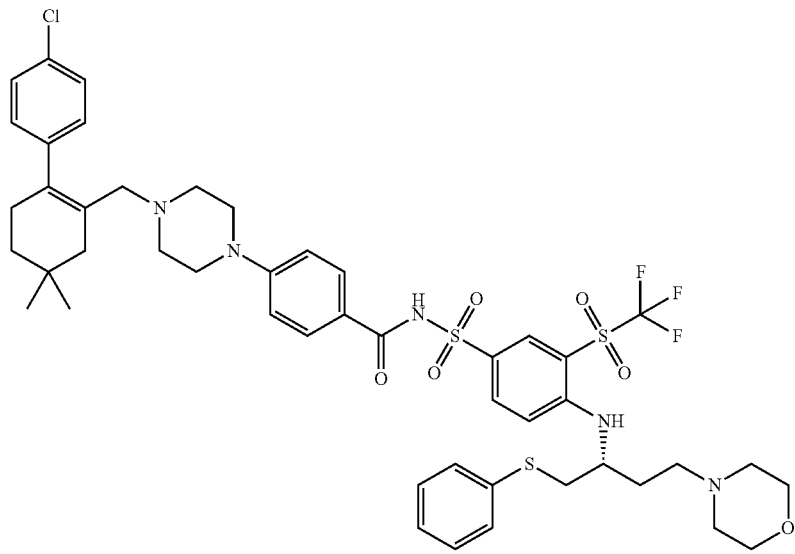 [SMILES: CC1(C)CCC(c2ccc(Cl)cc2)=C(CN2CCN(c3ccc(C(=O)NS(=O)(=O)c4ccc(N[C@H](CCN5CCOCC5)CSc5ccccc5)c(S(=O)(=O)C(F)(F)F)c4)cc3)CC2)C1]

4-(4-{[2-(4-Chlorophenyl)-5,5-dimethyl-1-cyclohexen-1-yl]methyl}-1-piperazinyl)-N-[(4-{[(2R)-4-(4-morpholinyl)-1-(phenylsulfanyl)-2-butanyl]amino}-3-[(trifluoromethyl)sulfonyl]phenyl)sulfonyl]benzamide.

As used herein, the terms "prevent" and "preventing" include the prevention of the recurrence, spread or onset. It is not intended that the present disclosure be limited to complete prevention. In some embodiments, the onset is delayed, or the severity of the disease is reduced.

As used herein, the terms "treat" and "treating" are not limited to the case where the subject (e.g. patient) is cured and the disease is eradicated. Rather, embodiments, of the present disclosure also contemplate treatment that merely reduces symptoms, and/or delays disease progression.

As used herein, the term "combination with" when used to describe administration with an additional treatment means that the agent may be administered prior to, together with, or after the additional treatment, or a combination thereof.

"Sample" or "biological sample" means biological material isolated from a subject. The biological sample may contain any biological material suitable for detecting the desired biomarkers, and may comprise cellular and/or non-cellular material from the subject. The sample can be isolated from any suitable biological tissue or fluid such as, for example, prostate tissue, blood, blood plasma, urine, or cerebral spinal fluid (CSF).

Although some assay formats will allow testing of peripheral biological fluid samples without prior processing of the sample, it is typical that peripheral biological fluid samples will be processed prior to testing. Processing generally takes the form of elimination of cells, such as platelets in blood samples, and may also include the elimination of certain proteins, such as certain clotting cascade proteins from blood. In some examples, the peripheral biological fluid sample is collected in a container comprising EDTA.

The process of comparing a measured value and control, e.g., normal or a reference value can be carried out in any convenient manner appropriate to the type of measured value and reference value for the protein at issue. As discussed above, measuring can be performed using quantitative or qualitative measurement techniques, and the mode of comparing a measured value and a reference value can vary depending on the measurement technology employed. For example, when a qualitative calorimetric assay is used to measure protein levels, the levels may be compared by visually comparing the intensity of the colored reaction product, or by comparing data from densitometric or spectrometric measurements of the colored reaction product (e.g., comparing numerical data or graphical data, such as bar charts, derived from the measuring device).

The process of comparing may be manual (such as visual inspection by the practitioner of the method) or it may be automated. For example, an assay device (such as a luminometer for measuring chemiluminescent signals) may include circuitry and software enabling it to compare a measured value with a reference value. Alternately, a separate device (e.g., a digital computer) may be used to compare the measured value(s) and the reference value(s). Automated devices for comparison may include stored reference values for the protein(s) being measured, or they may compare the measured value(s) with reference values that are derived from contemporaneously measured reference samples.

In some embodiments, the methods of the disclosure utilize simple or binary comparison between the measured level(s) and the reference level(s) (e.g., the comparison between a measured level and a reference level determines whether the measured level is higher or lower than the reference level).

As described herein, biological fluid samples may be measured quantitatively (absolute values) or qualitatively (relative values). In certain aspects of the disclosure, the comparison is performed to determine the magnitude of the difference between the measured and reference values (e.g., comparing the fold or percentage difference between the measured value and the reference value).

Succinate Ubiquinone Reductase Activity Predicts Cancer Sensitivity to Bcl-2 Family Inhibitors Depriving cells of glutamine enhanced binding of BIM to Bcl-2 thereby sensitizing myeloma cell lines and patient samples to the BH3 mimetic venetoclax (ABT-199), a highly selective, potent Bcl-2 antagonist. ABT-199 is however effective only in 40% of MM patients exhibiting the (11;14) translocation, warranting investigation of strategies to increase the applicability of ABT-199. Tests were performed to determine whether there were metabolic differences in ABT-199 sensitive t(11;14) and resistant cells that could inform us of a) predictors of sensitivity; and b) metabolic targets that could be inhibited to sensitize resistant cells to ABT-199. Given that, tumor cells differentially rely on glycolysis and mitochondrial oxidative phosphorylation oxygen consumption rates (OCR) were evaluated in ABT-199 sensitive and resistant MM lines. ABT-199 sensitive lines exhibited lower OCR in contrast to the resistant lines. Metabolite profiling and isotope tracing flux analyses of glutamine deprived myeloma cell lines revealed specific reduction of TCA cycle metabolites including succinate. TCA cycle intermediates are linked to mitochondrial respiration via electron transport chain (ETC) complexes (I-V). Among the five ETC complexes, only Complex II/succinate dehydrogenase (SDH) is directly connected to the TCA cycle and ETC. SDH facilitates the oxidation of succinate to fumarate in the TCA cycle through its subunit SDHA, and transfers the released electrons to ubiquinone via its SDHB, C and D subunits supporting the succinate ubiquinone reductase (SQR) activity of Complex II. Whether succinate dehydrogenase facilitates ABT-199 sensitization was investigated.

SDH ubiquinone reductase activity was evaluated in ABT-199 sensitive and resistant myeloma lines. ABT-199 sensitive cell lines had significantly lower SQR activity. Furthermore, inhibition of the SDH ubiquinone reductase with the Qp site inhibitor thenoyltrifluoroacetone (TTFA) sensitized resistant MM cells to ABT-199. Inhibition of Complex I with piericidin or the SDHA subunit with 3-NPA were not as effective in sensitizing MM to ABT-199. Protein expression and co-immunoprecipitation analyses demonstrated an induction of BIM and enhanced BIM-Bcl-2 binding upon SDH inhibition with TTFA. TTFA treated cells exhibited a reduction of Foxo3a phosphorylation and concomitant nuclear localization upon SDH inhibition suggestive of FOXO3a playing a role in BIM induction. TTFA+ ABT-199 co-treatment induced apoptosis in ABT-199 resistant myeloma patient cells without impacting viability of the associated normal populations. Thus, a tumor selective approach of metabolically-driven synthetic lethality relies on inhibition of the mitochondrial enzyme SDH and use of the Bcl-2 antagonist, e.g., ABT-199 for myeloma therapy. Experiments suggest SDH activity predicts ABT-199 sensitivity and can be interrogated in MM patients as a predictive marker of ABT-199 sensitivity particularly within t(11;14) patients currently being enrolled for ABT-199 treatment.

Experiments indicate that ABT-199 sensitive myeloma cell lines exhibit reduced basal mitochondrial respiration. Complex II-succinate ubiquinone reductase activity is reduced in ABT-199 sensitive myeloma cell lines and patient samples. Inhibition of Complex II at the ubiquinone binding site potently sensitizes resistant myeloma cells to ABT-199. Pro-apoptotic Bcl-2 family protein BIM, is required to sensitize glutamine-deprived or TTFA treated MM cells to ABT-199. Low succinate ubiquinone reductase activity correlates with venetoclax sensitivity in multiple myeloma.

Mitochondrial Complex II Inhibitor

Methods for identifying mitochondrial complex II inhibitors is found in Jones et al. A spectrophotometric coupled enzyme assay to measure the activity of succinate dehydrogenase. Anal Biochem, 2013, 442(1):19-23. In certain embodiments, the mitochondrial complex II inhibitor is any of the compounds disclosed herein or derivative thereof, e.g., compound disclosed herein optionally substituted with one or more substituent.

In certain embodiments, the mitochondrial complex II inhibitor is TTFA [4,4,4-trifluoro-1-(2-thienyl)-1,3-butanedione], atpenin A5 (3-[5,6-dichloro-2,4-dimethylhexanoyl]-4-hydroxy- 5,6-dimethoxy-1H-pyridin-2-one), atpenin A4 (3-[5-chloro-2,4-dimethylhexanoyl]-2-hydroxy-5,6-dimethoxy-1H-pyridin-4-one), thiabendazole, flutolanil (N-(3-propan-2-yloxyphenyl)-2-(trifluoromethyl)benzamide), harzianopyridone (2-Hydroxy-5,6-dimethoxy-3-[(2R)-2-methylhex-4-enoyl]-1H-pyridin-4-one), 1-(2,4-dihydroxy-5,6-dimethoxypyridin-3-yl)hexan-1-one, carboxin (5,6-dihydro-2-methyl-N-phenyl-1,4-oxathiin-3-carboxamide), and HQNO (2-heptyl-4-hydroxyquinoline N-oxide).

In certain embodiments, the mitochondrial complex II inhibitor is a compound of the following formula:

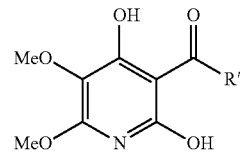

or salts thereof wherein R' is heptyl, octyl, nonyl, decyl, or dodecyl.

In certain embodiments, the mitochondrial complex II inhibitor is lonidamine (LND; 1-(2,4-dichlorobenzyl)-1H-indazole-3-carboxylic acid) or salts thereof.

Bcl-2 Inhibitors

In certain embodiments, the Bcl-2 inhibitor has the following formula:

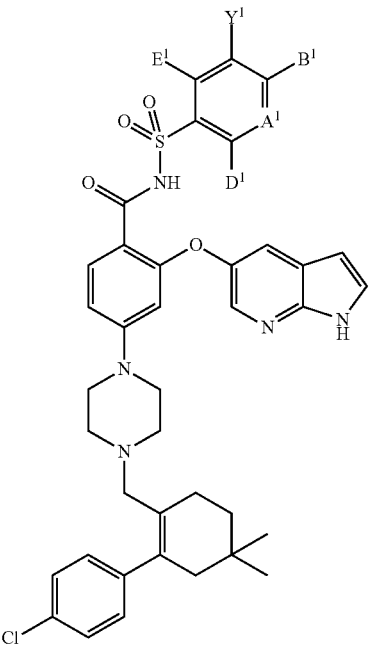

-continued

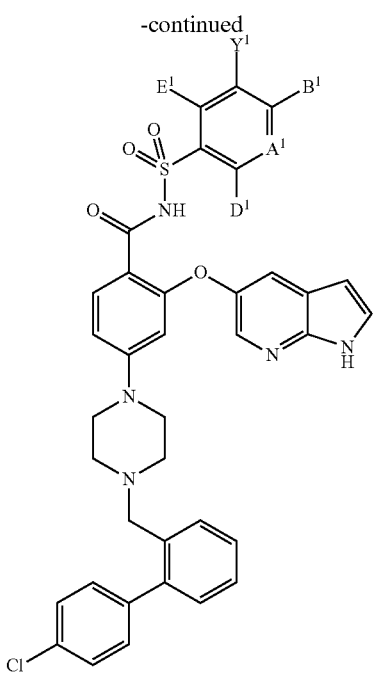

or pharmaceutically acceptable salt thereof, wherein
$A^1$ is $C(A^2)$;
$A^2$ is H, F, Br, I, or Cl;
$B^1$ is $R^1$, $OR^1$, $NHR^1$, $NHC(O)R^1$, F, Br, I, or Cl;
$D^1$ is H, F, Br, I, or Cl;
$E^1$ is H; and
$Y^1$ is H, CN, $NO_2$, F, Cl, Br, I, $CF_3$, $R^{17}$, $OR^{17}$, $SR^{17}$, $SO_2R^{17}$, or $C(O)NH_2$;
$R^1$ is $R^4$ or $R^5$;
$R^4$ is cycloalkyl or heterocycloalkyl;
$R^5$ is alkyl or alkynyl, each of which is unsubstituted or substituted with one or two or three substituents independently selected from the group consisting of $R^7$, $OR^7$, $NHR^7$, $N(R^7)_2$, CN, OH, F, Cl, Br, and I;
$R^7$ is $R^8$, $R^9$, $R^{10}$, or $R^{11}$;
$R^8$ is phenyl;
$R^9$ is heteroaryl;
$R^{10}$ is cycloalkyl, cycloalkenyl, or heterocycloalkyl; each of which is unfused or fused with $R^{10A}$; $R^{10A}$ is heteroarene;
$R^{11}$ is alkyl, which is unsubstituted or substituted with one or two or three substituents independently selected from the group consisting of $R^{12}$, $OR^{12}$, and $CF_3$;
$R^{12}$ is $R^{14}$ or $R^{16}$;
$R^{14}$ is heteroaryl;
$R^{16}$ is alkyl;
$R^{17}$ is alkyl or alkynyl, each of which is unsubstituted or substituted with one or two or three substituents independently selected from the group consisting of $R^{22}$, F, Cl, Br and I;
$R^{22}$ is heterocycloalkyl;
wherein the cyclic moieties represented by $R^4$, $R^8$, $R^{10}$, and $R^{22}$, are independently unsubstituted or substituted with one or two or three or four or five substituents independently selected from the group consisting of $R^{57A}$, $R^{27}$, $OR^{57}$, $SO_2R^{57}$, $C(O)R^{57}$, $C(O)OR^{57}$, $C(O)N(R^{57})_2$, $NH_2$, $NHR^{57}$, $N(R^{57})_2$, $NHC(O)R^{57}$, $NHS(O)_2R^{57}$, OH, CN, (O), F, Cl, Br and I;
$R^{57A}$ is spiroalkyl or spiroheteroalkyl;
$R^{57}$ is $R^{58}$, $R^{60}$, or $R^{61}$;
$R^{58}$ is phenyl;
$R^{60}$ is cycloalkyl or heterocycloalkyl;

$R^{61}$ is alkyl, which is unsubstituted or substituted with one or two or three substituents independently selected from the group consisting of $R^{62}$, $OR^{62}$, $N(R^{62})_2$, C(O)OH, CN, F, Cl, Br, and I;
$R^{62}$ is $R^{65}$ or $R^{66}$;
$R^{65}$ is cycloalkyl or heterocycloalkyl;
$R^{66}$ is alkyl, which is unsubstituted or substituted with $OR^{67}$;
$R^{67}$ is alkyl;
wherein the cyclic moieties represented by $R^{57A}$, $R^{58}$, and $R^{60}$ are unsubstituted or substituted with one or two or three or four substituents independently selected from the group consisting of $R^{68}$, F, Cl, Br, and I;
$R^{68}$ is $R^{71}$ or $R^{72}$;
$R^{71}$ is heterocycloalkyl; and
$R^{72}$ is alkyl, which is unsubstituted or substituted with one or two F.

In certain embodiments, the Bcl-2 inhibitor has the following formula:

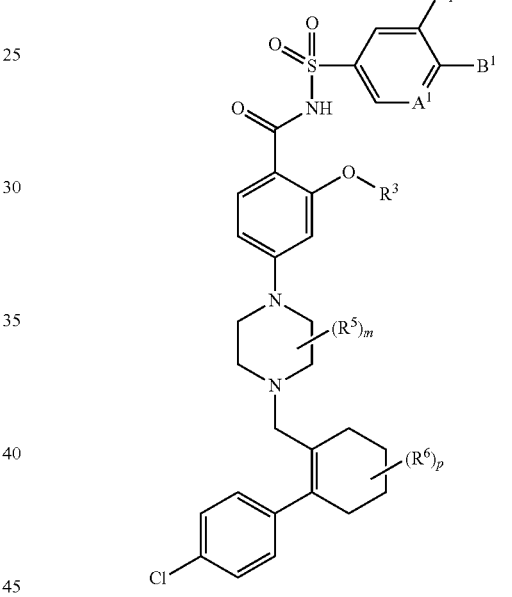

Or salts thereof wherein
$A^1$ is N or CH;
$B^1$ is $OR^1$ or $NHR^1$;
$Y^1$ is CN, $NO_2$, $CF_3$, F or Cl;
$R^1$ is $(CH_2)_nR^2$;
$R^2$ is cycloalkyl or heterocyclyl; wherein the heterocyclyl and cycloalkyl are optionally substituted with one or more independently selected $R^4$, $OR^4$, OH, CN, or F;
$R^3$ is heteroaryl; wherein the heteroaryl is optionally substituted with one or more independently selected $NH_2$, Cl, or F;
$R^4$ is alkyl, cycloalkyl, heterocyclyl, or spiroheterocyclyl; wherein the alkyl is optionally substituted with one or more F;
$R^5$ is hydrogen or deuterium;
each $R^6$ is independently selected from $CH_3$, spirocyclopropyl and OH;
m is 0, 1, 2, 3, 4, 5, or 6;
n is 0 or 1; and
p is 0, 1, or 2.

With regard to the various selective Bcl-2 inhibitor compounds encompassed by the current disclosure, it should be understood that variable moieties herein are represented by identifiers (capital letters with numerical and/or alphabetical superscripts) and may be specifically embodied.

It is meant to be understood that proper valences are maintained for all moieties and combinations thereof, that monovalent moieties having more than one atom are drawn from left to right and are attached through their left ends, and that divalent moieties are also drawn from left to right.

It is also meant to be understood that a specific embodiment of a variable moiety herein may be the same or different as another specific embodiment having the same identifier.

The term "alkyl" as used herein, means a straight or branched, saturated hydrocarbon chain containing from 1 to 10 carbon atoms. The term "Cx-Cy alkyl" means a straight or branched chain, saturated hydrocarbon containing x to y carbon atoms. For example "$C_2$-$C_{10}$ alkyl" means a straight or branched chain, saturated hydrocarbon containing 2 to 10 carbon atoms. Examples of alkyl include, but are not limited to, methyl, ethyl, n-propyl, iso-propyl, n-butyl, sec-butyl, iso-butyl, tert-butyl, n-pentyl, isopentyl, neopentyl, n-hexyl, 3-methylhexyl, 2,2-dimethylpentyl, 2,3-dimethylpentyl, n-heptyl, n-octyl, n-nonyl, and n-decyl.

The term "alkenyl" as used herein, means a straight or branched hydrocarbon chain containing from 2 to 10 carbons and containing at least one carbon-carbon double bond. The term "Cx-Cy alkyl" means a straight or branched hydrocarbon chain containing at least one carbon-carbon double bond containing x to y carbon atoms. The term "$C_2$-$C_4$ alkenyl" means an alkenyl group containing 2-4 carbon atoms. Representative examples of alkenyl include, but are not limited to buta-2,3-dienyl, ethenyl, 2-propenyl, 2-methyl-2-propenyl, 3-butenyl, 4-pentenyl, 5-hexenyl, 2-heptenyl, 2-methyl-1-heptenyl, and 3-decenyl.

The term "alkenylene" means a divalent group derived from a straight or branched chain hydrocarbon of 2 to 4 carbon atoms and contains at least one carbon-carbon double bond. The term "Cx-Cy alkylene" means a divalent group derived from a straight or branched hydrocarbon chain containing at least one carbon-carbon double bond and containing x to y carbon atoms. Representative examples of alkenylene include, but are not limited to, —CH═CH— and —CH$_2$CH═CH—.

The term "alkynyl" as used herein, means a straight or branched chain hydrocarbon group containing from 2 to 10 carbon atoms and containing at least one carbon-carbon triple bond. The term "Cx-Cy alkynyl" means a straight or branched chain hydrocarbon group containing from x to y carbon atoms. Representative examples of alkynyl include, but are not limited, to acetylenyl, 1-propynyl, 2-propynyl, 3-butynyl, 2-pentynyl, and 1-butynyl.

The term "alkynylene," as used herein, means a divalent radical derived from a straight or branched chain hydrocarbon group containing from 2 to 10 carbon atoms and containing at least one carbon-carbon triple bond.

The term "aryl" (alone or in combination with another term(s)) means an aromatic carbocyclyl containing from 6 to 14 carbon ring atoms. An aryl may be monocyclic or polycyclic (i.e., may contain more than one ring). In the case of polycyclic aromatic rings, only one ring the polycyclic system is required to be unsaturated while the remaining ring(s) may be saturated, partially saturated or unsaturated. Examples of aryls include phenyl, naphthalenyl, indenyl, indanyl, and tetrahydronaphthyl.

The term "carbocyclyl" (alone or in combination with another term(s)) means a saturated cyclic (i.e., "cycloalkyl"), partially saturated cyclic (i.e., "cycloalkenyl"), or completely unsaturated (i.e., "aryl") hydrocarbyl substituent containing from 3 to 14 carbon ring atoms ("ring atoms" are the atoms bound together to form the ring or rings of a cyclic substituent). A carbocyclyl may be a single-ring (monocyclic) or polycyclic ring structure.

A carbocyclyl may be a single ring structure, which typically contains from 3 to 8 ring atoms, more typically from 3 to 6 ring atoms, and even more typically 5 to 6 ring atoms. Examples of such single-ring carbocyclyls include cyclopropyl (cyclopropanyl), cyclobutyl (cyclobutanyl), cyclopentyl (cyclopentanyl), cyclopentenyl, cyclopentadienyl, cyclohexyl (cyclohexanyl), cyclohexenyl, cyclohexadienyl, and phenyl. A carbocyclyl may alternatively be polycyclic (i.e., may contain more than one ring). Examples of polycyclic carbocyclyls include bridged, fused, and spirocyclic carbocyclyls. In a spirocyclic carbocyclyl, one atom is common to two different rings. An example of a spirocyclic carbocyclyl substituent is spirocyclopropyl. In a spirocyclic carbocyclyl, one atom is common to two different rings. An example of a spirocyclic carbocyclyl is spiropentanyl. In a bridged carbocyclyl, the rings share at least two common non-adjacent atoms. Examples of bridged carbocyclyls include bicyclo[2.2.1]heptanyl, bicyclo[2.2.1]hept-2-enyl, and adamantanyl. In a fused-ring carbocyclyl system, two or more rings may be fused together, such that two rings share one common bond. Examples of two- or three-fused ring carbocyclyls include naphthalenyl, tetrahydronaphthalenyl (tetralinyl), indenyl, indanyl (dihydroindenyl), anthracenyl, phenanthrenyl, and decalinyl.

The term "cyclic moiety," as used herein, means benzene, phenyl, phenylene, cycloalkane, cycloalkyl, cycloalkylene, cycloalkene, cycloalkenyl, cycloalkenylene, cycloalkyne, cycloalkynyl, cycloalkynylene, heteroarene, heteroaryl, heterocycloalkane, heterocycloalkyl, heterocycloalkene, heterocycloalkenyl and spiroalkyl.

The term "cycloalkylene" or cycloalkyl" or "cycloalkane" as used herein, means a monocyclic or bridged hydrocarbon ring system. The monocyclic cycloalkyl is a carbocyclic ring system containing three to eight carbon atoms, zero heteroatoms and zero double bonds. Examples of monocyclic ring systems include cyclopropyl, cyclobutyl, cyclopentyl, cyclohexyl, cycloheptyl, and cyclooctyl. The monocyclic ring may contain one or two alkylene bridges, each consisting of one, two, or three carbon atoms, each linking two non-adjacent carbon atoms of the ring system. Non-limiting examples of such bridged cycloalkyl ring systems include bicyclo[3.1.1]heptane, bicyclo[2.2.1]heptane, bicyclo[2.2.2]octane, bicyclo[3.2.2]nonane, bicyclo[3.3.1]nonane, bicyclo[4.2.1]nonane, tricyclo[3.3.1.0.sup.3,7]nonane (octahydro-2,5-methanopentalene or noradamantane), and tricyclo[3.3.1.1.sup.3,7]decane (adamantane). The monocyclic and bridged cycloalkyl can be attached to the parent molecular moiety through any substitutable atom contained within the ring system.

The term "cycloalkenylene," or "cycloalkenyl" or "cycloalkene" as used herein, means a monocyclic or a bridged hydrocarbon ring system. The monocyclic cycloalkenyl has four-, five-, six-, seven- or eight carbon atoms and zero heteroatoms. The four-membered ring systems have one double bond, the five- or six-membered ring systems have one or two double bonds, and the seven- or eight-membered ring systems have one, two, or three double bonds. Representative examples of monocyclic cycloalkenyl groups include, but are not limited to, cyclobutenyl, cyclopentenyl, cyclohexenyl, cycloheptenyl, and cyclooctenyl. The monocyclic cycloalkenyl ring may contain one or two alkylene bridges, each consisting of one, two, or three carbon atoms, each linking two non-adjacent carbon atoms of the ring system. Representative examples of the bicyclic cycloalkenyl groups include, but are not limited to, 4,5,6,7-tetrahydro-3aH-indene, octahydronaphthalenyl, and 1,6-dihydro-pentalene. The monocyclic and bicyclic cycloalkenyl can be attached to the parent molecular moiety through any substitutable atom contained within the ring systems.

The term "cycloalkyne," or "cycloalkynyl," or "cycloalkynylene," as used herein, means a monocyclic or a bridged hydrocarbon ring system. The monocyclic cycloalkynyl has eight or more carbon atoms, zero heteroatoms, and one or more triple bonds. The monocyclic cycloalkynyl ring may contain one or two alkylene bridges, each consisting of one, two, or three carbon atoms, each linking two non-adjacent carbon atoms of the ring system. The monocyclic and bridged cycloalkynyl can be attached to the parent molecular moiety through any substitutable atom contained within the ring systems.

The term "heteroarene," or "heteroaryl," or "heteroarylene," as used herein, means a five-membered or six-membered aromatic ring having at least one carbon atom and one or more than one independently selected nitrogen, oxygen or sulfur atom. The heteroarenes of this disclosure are connected through any adjacent atoms in the ring, provided that proper valences are maintained. Specifically, the term "heteroaryl" (alone or in combination with another term(s)) means an aromatic heterocyclyl containing from 5 to 14 ring atoms. A heteroaryl may be a single ring or 2 or 3 fused rings. Examples of heteroaryl substituents include 6-membered ring substituents such as pyridyl, pyrazyl, pyrimidinyl, pyridazinyl, and 1,3,5-, 1,2,4- or 1,2,3-triazinyl; 5-membered ring substituents such as imidazyl, furanyl, thiophenyl, pyrazolyl, oxazolyl, isoxazolyl, thiazolyl, 1,2,3-, 1,2,4-, 1,2,5-, or 1,3,4-oxadiazolyl and isothiazolyl; 6/5-membered fused ring substituents such as benzothiofuranyl, benzisoxazolyl, benzoxazolyl, imidazolyl, indolyl, benzoimidazolyl, pyrrolo[2,3-b]pyridinyl, purinyl, and anthranilyl; and 6/6-membered fused rings such as benzopyranyl, quinolinyl, isoquinolinyl, cinnolinyl, quinazolinyl, and benzoxazinyl.

The term "heterocyclyl" (alone or in combination with another term(s)) means a saturated (i.e., "heterocycloalkyl"), partially saturated (i.e., "heterocycloalkenyl"), or completely unsaturated (i.e., "heteroaryl") ring structure containing a total of 3 to 14 ring atoms. At least one of the ring atoms is a heteroatom (i.e., oxygen, nitrogen, or sulfur), with the remaining ring atoms being independently selected from the group consisting of carbon, oxygen, nitrogen, and sulfur. A heterocyclyl may be a single-ring (monocyclic) or polycyclic ring structure. A heterocyclyl may be a single ring, which typically contains from 3 to 7 ring atoms, more typically from 3 to 6 ring atoms, and even more typically 5 to 6 ring atoms. Examples of single-ring heterocyclyls include furanyl, dihydrofuranyl, tetrahydrofuranyl, tetrahydropyranyl, thiophenyl (thiofuranyl), dihydrothiophenyl, tetrahydrothiophenyl, pyrrolyl, pyrrolinyl, pyrrolidinyl, imidazolyl, imidazolinyl, imidazolidinyl, pyrazolyl, pyrazolinyl, pyrazolidinyl, triazolyl, tetrazolyl, oxazolyl, oxazolidinyl, isoxazolidinyl, isoxazolyl, thiazolyl, isothiazolyl, thiazolinyl, isothiazolinyl, thiazolidinyl, isothiazolidinyl, thiodiazolyl, oxadiazolyl (including 1,2,3-oxadiazolyl, 1,2,4-oxadiazolyl, 1,2,5-oxadiazolyl (furazanyl), or 1,3,4-oxadiazolyl), oxatriazolyl (including 1,2,3,4-oxatriazolyl or 1,2,3,5-oxatriazolyl), oxetanyl, dioxazolyl (including 1,2,3-dioxazolyl, 1,2,4-dioxazolyl, 1,3,2-dioxazolyl, or 1,3,4-dioxazolyl), oxathiazolyl, oxathiolyl, oxathiolanyl, pyranyl, dihydropyranyl, thiopyranyl, tetrahydrothiopyranyl, pyridinyl (azinyl), piperidinyl, diazinyl (including pyridazinyl (1,2-diazinyl), pyrimidinyl (1,3-diazinyl), or pyrazinyl (1,4-diazinyl)), piperazinyl, triazinyl (including 1,3,5-triazinyl, 1,2,4-triazinyl, and 1,2,3-triazinyl)), oxazinyl (including 1,2-oxazinyl, 1,3-oxazinyl, or 1,4-oxazinyl)), oxathiazinyl (including 1,2,3-oxathiazinyl, 1,2,4-oxathiazinyl, 1,2,5-oxathiazinyl, or 1,2,6-oxathiazinyl)), oxadiazinyl (including 1,2,3-oxadiazinyl, 1,2,4-oxadiazinyl, 1,4,2-oxadiazinyl, or 1,3,5-oxadiazinyl)), morpholinyl, azepinyl, oxepinyl, thiepinyl, and diazepinyl.

A heterocyclyl may alternatively be polycyclic (i.e., may contain more than one ring). Examples of polycyclic heterocyclyls include bridged, fused, and spirocyclic heterocyclyls. In a spirocyclic heterocyclyl, one atom is common to two different rings. Examples of spirocyclic heterocyclyls include 2-oxaspiro[3.5]nonanyl. Examples of polycyclic heterocyclyls include bridged, fused, and spirocyclic heterocyclyls. In a spirocyclic heterocyclyl, one atom is common to two different rings. Examples of spirocyclic heterocyclyl include 2-oxaspiro[3.5]nonanyl. In a bridged heterocyclyl, the rings share at least two common non-adjacent atoms. In a fused-ring heterocyclyl, two or more rings may be fused together, such that two rings share one common bond. Examples of fused ring heterocyclyls containing two or three rings include indolizinyl, pyranopyrrolyl, 4H-quinolizinyl, purinyl, naphthyridinyl, pyrrolo[2,3-b]pyridinyl, pyridopyridinyl (including pyrido[3,4-b]-pyridinyl, pyrido[3,2-b]-pyridinyl, or pyrido[4,3-b]-pyridinyl), and pteridinyl. Other examples of fused-ring heterocyclyls include benzo-fused heterocyclyls, such as indolyl, indazoyl, isoindolyl (isobenzazolyl, pseudoisoindolyl), indoleninyl (pseudoindolyl), isoindazolyl (benzpyrazolyl), benzoimidazolyl, benzazinyl (including quinolinyl (1-benzazinyl) or isoquinolinyl (2-benzazinyl)), phthalazinyl, quinoxalinyl, quinazolinyl, benzodiazinyl (including cinnolinyl (1,2-benzodiazinyl) or quinazolinyl (1,3-benzodiazinyl)), benzopyranyl (including chromanyl or isochromanyl), benzoxazinyl (including 1,3,2-benzoxazinyl, 1,4,2-benzoxazinyl, 2,3,1-benzoxazinyl, or 3,1,4-benzoxazinyl), and benzisoxazinyl (including 1,2-benzisoxazinyl or 1,4-benzisoxazinyl).

The term "heterocycloalkyl" (alone or in combination with another term(s)) means a saturated heterocyclyl.

The term "heterocycloalkene," or "heterocycloalkenyl," or "heterocycloalkenylene," as used herein, means monocyclic or bridged three-, four-, five-, six-, seven-, or eight-membered ring containing at least one heteroatom independently selected from the group consisting of 0, N, and S and one or more double bonds. The monocyclic and bridged heterocycloalkene are connected to the parent molecular moiety through any substitutable carbon atom or any substitutable nitrogen atom contained within the rings. The nitrogen and sulfur heteroatoms in the heterocycle rings may optionally be oxidized and the nitrogen atoms may optionally be quarternized. Representative examples of heterocycloalkene groups include, but are not limited to, tetrahydrooxocinyl, 1,4,5,6-tetrahydropyridazinyl, 1,2,3,6-tetrahydropyridinyl, dihydropyranyl, imidazolinyl, isothiazolinyl, oxadiazolinyl, isoxazolinyl, oxazolinyl, pyranyl, pyrazolinyl, pyrrolinyl, thiadiazolinyl, thiazolinyl, and thiopyranyl.

The term "phenylene," as used herein, means a divalent radical formed by removal of a hydrogen atom from phenyl.

The term "spiroalkyl," as used herein, means alkylene, both ends of which are attached to the same carbon atom and is exemplified by $C_2$-spiroalkyl, $C_3$-spiroalkyl, $C_4$-spiroalkyl, $C_5$-spiroalkyl, $C_6$-spiroalkyl, $C_7$-spiroalkyl, $C_8$-spiroalkyl, $C_9$-spiroalkyl and the like.

The term "spiroheteroalkyl," as used herein, means spiroalkyl having one or two $CH_2$ moieties replaced with independently selected O, C(O), CNOH, $CNOCH_3$, S, S(O), $SO_2$ or NH and one or two CH moieties unreplaced or replaced with N.

The term "spiroheteroalkenyl," as used herein, means spiroalkenyl having one or two $CH_2$ moieties replaced with independently selected O, C(O), CNOH, $CNOCH_3$, S, S(O), $SO_2$ or NH and one or two CH moieties unreplaced or replaced with N and also means spiroalkenyl having one or two $CH_2$ moieties unreplaced or replaced with independently selected O, C(O), CNOH, $CNOCH_3$, S, S(O), $SO_2$ or NH and one or two CH moieties replaced with N.

The term, "spirocyclo," as used herein, means two substituents on the same carbon atom that, together with the carbon atom to which they are attached, form a cycloalkane, heterocycloalkane, cycloalkene, or heterocycloalkene ring.

As stated, the selective Bcl-2 inhibitor compounds of the current disclosure encompass all possible combinations of the substituents for the genus compound of the formulas. Suitable examples of compounds that fall within the scope of the current disclosure include, but are not limited to, N-({5-chloro-6-[(4-fluorotetrahydro-2H-pyran-4-yl) methoxy]pyridin-3-yl}sulfonyl)-4-(4-{[2-(4-chlorophenyl)-4,4-dimethylcyclohex-1-en-1-yl]methyl}piperazin-1-yl)-2-[(6-fluoro-1H-indazol-4-yl)oxy]benzamide;

4-(4-{[2-(4-chlorophenyl)-4,4-dimethylcyclohex-1-en-1-yl]methyl}piperazin-1-yl)-N-{[4-({[(2S)-4-cyclopropylmorpholin-2-yl]methyl}amino)-3-nitrophenyl]sulfonyl}-2-(1H-pyrrolo[2,3-b]pyridin-5-yloxy)benzamide;

N-({5-chloro-6-[(4-fluorotetrahydro-2H-pyran-4-yl) methoxy]pyridin-3-yl}sulfonyl)-4-(4-{[2-(4-chlorophenyl)-4,4-dimethylcyclohex-1-en-1-yl]methyl}piperazin-1-yl)-2-(1H-indazol-4-yloxy)benzamide;

4-(4-{[2-(4-chlorophenyl)-4,4-dimethylcyclohex-1-en-1-yl]methyl}piperazin-1-yl)-2-[(6-fluoro-1H-indol-5-yl)oxy]-N-({4-[(4-fluorotetrahydro-2H-pyran-4-yl)methoxy]-3-nitrophenyl}sulfonyl)benzamide;

4-(4-{[2-(4-chlorophenyl)-4,4-dimethylcyclohex-1-en-1-yl]methyl}piperazin-1-yl)-N-[(4-{[(4,4-difluorocyclohexyl)methyl]amino}-3-nitrophenyl)sulfonyl]-2-(1H-pyrrolo[2,3-b]pyridin-5-yloxy)benzamide;

2-(1H-benzimidazol-4-yloxy)-4-(4-{[2-(4-chlorophenyl)-4,4-dimethylcyclohex-1-en-1-yl]methyl}piperazin-1-yl)-N-({5-fluoro-6-[(4-fluorotetrahydro-2H-pyran-4-yl) methoxy]pyridin-3-yl}sulfonyl)benzamide;

4-(4-{[2-(4-chlorophenyl)-4,4-dimethylcyclohex-1-en-1-yl]methyl}piperazin-1-yl)-N-({3-nitro-4-[(tetrahydro-2H-pyran-4-ylmethyl)amino]phenyl}sulfony-1)-2-(1H-pyrrolo[2,3-b]pyridin-5-yloxy)benzamide;

N-({3-chloro-4-[(4-fluorotetrahydro-2H-pyran-4-yl) methoxy]phenyl}sulfonyl)-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide;

2-(1H-benzimidazol-4-yloxy)-4-(4-{[2-(4-chlorophenyl)-4,4-dimethylcyclohex-1-en-1-yl]methyl}piperazin-1-yl)-N-[(4-{[(cyanocyclohexyl)methyl]amino}-3-nitrophenyl)sulfonyl]benzamide;

N-({5-chloro-6-[(cis-4-hydroxy-4-methylcyclohexyl) methoxy]pyridin-3-yl}sulfonyl)-4-(4-{[2-(4-chlorophenyl)-4,4-dimethylcyclohex-1-en-1-yl]methyl}piperazin-1-yl)-2-(1H-indazol-4-yloxy)benzamide;

N-[(3-chloro-4-{[4-fluoro-1-(oxetan-3-yl)piperidin-4-yl] methoxy}phenyl)sulfonyl]-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-({5-cyano-6-[(4-fluorotetrahydro-2H-pyran-4-yl)methoxy]pyridin-3-yl}sulfonyl)-2-(1H-indol-4-yloxy)benzamide;

4-(4-{[2-(4-chlorophenyl)-4,4-dimethylcyclohex-1-en-1-yl]methyl}piperazin-1-yl)-N-[(4-{[(4-fluorotetrahydro-2H-pyran-4-yl)methyl]amino}-3-nitrophenyl)sulfonyl]-2-(1H-pyrrolo[2,3-b]pyridin-5-yloxy)benzamide;

N-({3-chloro-4-[(4-fluorotetrahydro-2H-pyran-4-yl) methoxy]phenyl}sulfonyl)-4-(4-{[2-(4-chlorophenyl)-4,4-dimethylcyclohex-1-en-1-yl]methyl}piperazin-1-yl)-2-(1H-indazol-4-yloxy)benzamide;

4-(4-{[2-(4-chlorophenyl)-4,4-dimethylcyclohex-1-en-1-yl]methyl}piperazin-1-yl)-N-({5-fluoro-6-[(4-fluorotetrahydro-2H-pyran-4-yl)methoxy]pyridin-3-yl}sulfonyl)-2-(1H-indazol-4-yloxy)benzamide;

4-(4-{[2-(4-chlorophenyl)-4,4-dimethylcyclohex-1-en-1-yl]methyl}piperazin-1-yl)-N-{[4-({[(2R)-4-cyclopropylmorpholin-2-yl]methyl}amino)-3-nitrophenyl]sulfonyl}-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-[(4-{[(trans-4-cyanocyclohexyl)methyl]amino}-3-nitrophenyl)sulfonyl]-2-(1H-pyrrolo[2,3-b]pyridin-5-yloxy)benzamide;

Trans-2-[(6-amino-5-chloropyridin-3-yl)oxy]-4-(4-{[2-(4-chlorophenyl)-4,4-dimethylcyclohex-1-en-1-yl] methyl}piperazin-1-yl)-N-({4-[(4-morpholin-4-ylcyclohexyl)amino]-3-nitrophenyl}sulfonyl)benzamide;

4-(4-{[2-(4-chlorophenyl)-4,4-dimethylcyclohex-1-en-1-yl]methyl}piperazin-1-yl)-N-{[4-({(3R)-1-[2-fluoro-1-(fluoromethyl)ethyl]pyrrolidin-3-yl}amino)-3-nitrophenyl]sulfonyl}-2-(1H-pyrrolo[2,3-b]pyridin-5-yloxy) benzamide;

Trans-N-({5-chloro-6-[(4-hydroxycyclohexyl)methoxy] pyridin-3-yl}sulfonyl)-4-(4-{[2-(4-chlorophenyl)-4,4-dimethylcyclohex-1-en-1-yl]methyl}piperazin-1-yl)-2-(1H-indazol-4-yloxy)benzamide;

N-({3-chloro-4-[(trans-hydroxycyclohexyl)methoxy] phenyl}sulfonyl)-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide;

N-({5-chloro-6-[(trans-4-hydroxycyclohexyl)methoxy] pyridin-3-yl}sulfonyl)-4-(4-{[2-(4-chlorophenyl)-4,4-dimethylcyclohex-1-en-1-yl]methyl}piperazin-1-yl)-2-[(6-fluoro-1H-indazol-4-yl)oxy]benzamide;

2-[(6-amino-5-chloropyridin-3-yl)oxy]-4-(4-{[2-(4-chlorophenyl)-4,4-dimethylcyclohex-1-en-1-yl] methyl}piperazin-1-yl)-N-[(4-{[trans-4-(morpholin-4-yl) cyclohexyl]amino}-3-nitrophenyl)sulfonyl]benzamide;

4-(4-{[2-(4-chlorophenyl)-4,4-dimethylcyclohex-1-en-1-yl] methyl}piperazin-1-yl)-N-[(4-{[(cis-4-hydroxy-4-methylcyclohexyl)methyl]amino}-3-nitrophenyl)sulfonyl]-2-(1H-pyrrolo[2,3-b]pyridin-5-yloxy)benzamide;

4-(4-{[2-(4-chlorophenyl)-4,4-dimethylcyclohex-1-en-1-yl] methyl}piperazin-1-yl)-N-({5-cyano-6-[(4-fluorotetrahydro-2H-pyran-4-yl)methoxy]pyridin-3-yl}sulfonyl)-2-(1H-indazol-4-yloxy)benzamide;

N-[(5-chloro-6-{[4-fluoro-1-(oxetan-3-yl)piperidin-4-yl] methoxy}pyridin-3-yl)sulfonyl]-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide;

2-[(6-amino-5-chloropyridin-3-yl)oxy]-4-(4-{[2-(4-chlorophenyl)-4,4-dimethylcyclohex-1-en-1-yl]

methyl}piperazin-1-yl)-N-({3-nitro-4-[(tetrahydro-2H-pyran-4-ylmethyl)amino]phenyl}sulfonyl)benzamide;

4-(4-{[2-(4-chlorophenyl)-4,4-dimethylcyclohex-1-en-1-yl]methyl}piperazin-1-yl)-N-({4-[(4-methylpiperazin-1-yl)amino]-3-nitrophenyl}sulfonyl)-2-(1H-pyrrolo[2,3-b]pyridin-5-yloxy)benzamide;

Trans-4-(4-{[2-(4-chlorophenyl)-4,4-dimethylcyclohex-1-en-1-yl]methyl}piperazin-1-yl)-N-[(4-{[(4-methoxycyclohexyl)methyl]amino}-3-nitrophenyl)sulfonyl]-2-(1H-pyrrolo[2,3-b]pyridin-5-yloxy)benzamide;

Trans-4-(4-{[2-(4-chlorophenyl)-4,4-dimethylcyclohex-1-en-1-yl]methyl}piperazin-1-yl)-N-({4-[(4-morpholin-4-ylcyclohexyl)amino]-3-nitrophenyl}sulfonyl)-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-({4-[(4-fluorotetrahydro-2H-pyran-4-yl)methoxy]-3-nitrophenyl}sulfonyl)-2-(1H-pyrrolo[2,3-b]pyridin-5-yloxy)benzamide;

2-[(6-amino-5-chloropyridin-3-yl)oxy]-4-(4-{[2-(4-chlorophenyl)-4,4-dimethylcyclohex-1-en-1-yl]methyl}piperazin-1-yl)-N-[(4-{[(3R)-1-(2,2-difluoroethyl)pyrrolidin-3-yl]amino}-3-nitrophenyl)sulfonyl]benzamide;

N-({5-chloro-6-[(trans-4-hydroxy-4-methylcyclohexyl)methoxy]pyridin-3-yl}sulfonyl)-4-(4-{[2-(4-chlorophenyl)-4,4-dimethylcyclohex-1-en-1-yl]methyl}piperazin-1-yl)-2-(1H-indazol-4-yloxy)benzamide;

N-({5-chloro-6-[(cis-1-fluoro-4-hydroxy-4-methylcyclohexyl)methoxy]pyridin-3-yl}sulfonyl)-4-(4-{[2-(4-chlorophenyl)-4,4-dimethylcyclohex-1-en-1-yl]methyl}piperazin-1-yl)-2-(1H-indazol-4-yloxy)benzamide;

2-[(6-amino-5-chloropyridin-3-yl)oxy]-4-(4-{[2-(4-chlorophenyl)-4,4-dimethylcyclohex-1-en-1-yl]methyl}piperazin-1-yl)-N-[(4-{[(4-methoxycyclohexyl)methyl]amino}-3-nitrophenyl)sulfonyl]benzamide;

N-({5-chloro-6-[(trans-1-fluoro-4-hydroxy-4-methylcyclohexyl)methoxy]pyridin-3-yl}sulfonyl)-4-(4-{[2-(4-chlorophenyl)-4,4-dimethylcyclohex-1-en-1-yl]methyl}piperazin-1-yl)-2-(1H-indazol-4-yloxy)benzamide;

4-(4-{[2-(4-chlorophenyl)-4,4-dimethylcyclohex-1-en-1-yl]methyl}piperazin-1-yl)-N-[(4-{[(trans-4-hydroxy-4-methylcyclohexyl)methyl]amino}-3-nitrophenyl)sulfonyl]-2-(1H-pyrrolo[2,3-b]pyridin-5-yloxy)benzamide;

2-[(3-amino-1H-indazol-4-yl)oxy]-4-(4-{[2-(4-chlorophenyl)-4,4-dimethylcyclohex-1-en-1-yl]methyl}piperazin-1-yl)-N-[(4-{[(trans-4-methoxycyclohexyl)methyl]amino}-3-nitrophenyl)sulfonyl]benzamide;

4-(4-{[2-(4-chlorophenyl)-4,4-dimethylcyclohex-1-en-1-yl]methyl}piperazin-1-yl)-N-({3-nitro-4-[(2-oxaspiro[3.5]non-7-ylmethyl)amino]phenyl}sulfonyl)-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-({5-cyano-6-[(trans-4-hydroxy-4-methylcyclohexyl)methoxy]pyridin-3-yl}sulfonyl)-2-(1H-indazol-4-yloxy)benzamide;

4-(4-{[2-(4-chlorophenyl)-4,4-dimethylcyclohex-1-en-1-yl]methyl}piperazin-1-yl)-2-[(6-fluoro-1H-indol-5-yl)oxy]-N-{[3-nitro-4-({[4-(oxetan-3-yl)morpholin-2-yl]methyl}amino)phenyl]sulfonyl}benzamide;

N-({5-chloro-6-[(trans-4-hydroxy-4-methylcyclohexyl)methoxy]pyridin-3-yl}sulfonyl)-4-(4-{[2-(4-chlorophenyl)-4,4-dimethylcyclohex-1-en-1-yl]methyl}piperazin-1-yl)-2-[(6-fluoro-1H-indol-4-yl)oxy]benzamide;

4-(4-{[2-(4-chlorophenyl)-4,4-dimethylcyclohex-1-en-1-yl]methyl}piperazin-1-yl)-N-[(5-cyano-6-{[4-fluoro-1-(oxetan-3-yl)piperidin-4-yl]methoxy}pyridin-3-yl)sulfonyl]-2-(1H-pyrrolo[2,3-b]pyridin-5-yloxy)benzamide;

2-[(6-amino-5-chloropyridin-3-yl)oxy]-4-(4-{[2-(4-chlorophenyl)-4,4-dimethylcyclohex-1-en-1-yl]methyl}piperazin-1-yl)-N-[(4-{[(4-hydroxycyclohexyl)methyl]amino}-3-nitrophenyl)sulfonyl]benzamide;

N-({5-chloro-6-[(trans-4-hydroxy-4-methylcyclohexyl)methoxy]pyridin-3-yl}sulfonyl)-2-[(3-chloro-1H-indazol-4-yl)oxy]-4-(4-{[2-(4-chlorophenyl)-4,4-dimethylcyclohex-1-en-1-yl]methyl}piperazin-1-yl)benzamide;

4-[4-{[2-(4-chlorophenyl)-4,4-dimethylcyclohex-1-en-1-yl]methyl}($^2H_8$)piperazin-1-yl]-N-({3-nitro-4-[(tetrahydro-2H-pyran-4-ylmethyl)amino]phenyl}sulfonyl)-2-(1H-pyrrolo[2,3-b]pyridin-5-yloxy)benzamide;

N-({5-chloro-6-[(trans-1-fluoro-4-hydroxy-4-methylcyclohexyl)methoxy]pyridin-3-yl}sulfonyl)-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-[(6-{[(cis-4-hydroxy-4-methylcyclohexyl)methyl]amino}-5-nitropyridin-3-yl)sulfonyl]-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-({5-nitro-6-[(tetrahydro-2H-pyran-4-ylmethyl)amino]pyridin-3-yl}sulfonyl)-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-({6-[(trans-4-hydroxy-4-methylcyclohexyl)methoxy]-5-(trifluoromethyl)pyridin-3-yl}sulfonyl)-2-(1H-indazol-4-yloxy)benzamide;

4-(4-{[2-(4-chlorophenyl)-4,4-dimethylcyclohex-1-en-1-yl]methyl}piperazin-1-yl)-N-[(4-{[(cis-4-ethyl-4-hydroxycyclohexyl)methyl]amino}-3-nitrophenyl)sulfonyl]-2-(1H-pyrrolo[2,3-b]pyridin-5-yloxy)benzamide; and 4-(4-{[2-(4-chlorophenyl)-4,4-dimethylcyclohex-1-en-1-yl]methyl}piperazin-1-yl)-2-(1H-indol-5-yloxy)-N-({3-nitro-4-[(tetrahydro-2H-pyran-4-ylmethyl)amino]phenyl}sulfonyl)benzamide.

Formulations

Further, the methods of the disclosure include administering compounds having the chemical names or formula reported herein with or without an excipient. Excipients include, for example, encapsulating materials or additives such as absorption accelerators, antioxidants, binders, buffers, coating agents, coloring agents, diluents, disintegrating agents, emulsifiers, extenders, fillers, flavoring agents, humectants, lubricants, perfumes, preservatives, propellants, releasing agents, sterilizing agents, sweeteners, solubilizers, wetting agents and mixtures thereof.

Excipients for preparation of compositions comprising a compound having the formula to be administered orally in solid dosage form include, for example, agar, alginic acid, aluminum hydroxide, benzyl alcohol, benzyl benzoate, 1,3-butylene glycol, carbomers, castor oil, cellulose, cellulose acetate, cocoa butter, corn starch, corn oil, cottonseed oil, cross-povidone, diglycerides, ethanol, ethyl cellulose, ethyl laureate, ethyl oleate, fatty acid esters, gelatin, germ oil, glucose, glycerol, groundnut oil, hydroxypropylmethyl cellulose, isopropanol, isotonic saline, lactose, magnesium hydroxide, magnesium stearate, malt, mannitol, monoglycerides, olive oil, peanut oil, potassium phosphate salts, potato starch, povidone, propylene glycol, Ringer's solution, safflower oil, sesame oil, sodium carboxymethyl cellulose, sodium phosphate salts, sodium lauryl sulfate, sodium sorbitol, soybean oil, stearic acids, stearyl fumarate, sucrose, surfactants, talc, tragacanth, tetrahydrofurfuryl alcohol, triglycerides, water, and mixtures thereof. Excipients for preparation of compositions comprising a compound of this disclosure having the formula to be administered ophthalmically or orally in liquid dosage forms include, for example, 1,3-butylene glycol, castor oil, corn oil, cottonseed oil, ethanol, fatty acid esters of sorbitan, germ oil, groundnut oil, glycerol, isopropanol, olive oil, polyethylene glycols, propylene glycol, sesame oil, water and mixtures thereof. Excipients for preparation of compositions comprising a compound of this disclosure having the formula to be administered osmotically include, for example, chlorofluorohydrocarbons, ethanol, water and mixtures thereof. Excipients for preparation of compositions comprising a compound of this disclosure having the formula to be administered parenterally include, for example, 1,3-butanediol, castor oil, corn oil, cottonseed oil, dextrose, germ oil, groundnut oil, liposomes, oleic acid, olive oil, peanut oil, Ringer's solution, safflower oil, sesame oil, soybean oil, U.S.P. or isotonic sodium chloride solution, water and mixtures thereof. Excipients for preparation of compositions comprising a compound of this disclosure having the formula to be administered rectally or vaginally include, for example, cocoa butter, polyethylene glycol, wax and mixtures thereof.

The compounds used in the methods of the current disclosure may also include a pharmaceutically acceptable salt form of a compound having the formula. The phrase "pharmaceutically acceptable salt(s)", as used herein, means those salts of the selective Bcl-2 inhibitors of the disclosure that are safe and effective for administration to a patient and that do not adversely affect the therapeutic qualities of the compound. Pharmaceutically acceptable salts include salts of acidic or basic groups present in compounds of the disclosure. Pharmaceutically acceptable acid addition salts include, but are not limited to, hydrochloride, hydrobromide, hydroiodide, nitrate, sulfate, bisulfate, phosphate, acid phosphate, isonicotinate, acetate, lactate, salicylate, citrate, tartrate, pantothenate, bitartrate, ascorbate, succinate, maleate, gentisinate, fumarate, gluconate, glucaronate, saccharate, formate, benzoate, glutamate, methanesulfonate, ethanesulfonate, benzensulfonate, p-toluenesulfonate and pamoate (i.e., 1,1'-methylene-bis-(2-hydroxy-3-naphthoate)) salts. Certain compounds of the disclosure can form pharmaceutically acceptable salts with various amino acids. Suitable base salts include, but are not limited to, aluminum, calcium, lithium, magnesium, potassium, sodium, zinc, and diethanolamine salts. For a review on pharmaceutically acceptable salts see Berge et al., 66 J. Pharm. Sci., 1-19 (1977), incorporated herein by reference, in its entirety.

The compounds used in the methods of the current disclosure may also comprise geometric isomers. Compounds of this disclosure may contain carbon-carbon double bonds or carbon-nitrogen double bonds in the E or Z configuration, wherein the term "E" represents higher order substituents on opposite sides of the carbon-carbon or carbon-nitrogen double bond and the term "Z" represents higher order substituents on the same side of the carbon-carbon or carbon-nitrogen double bond as determined by the Cahn-Ingold-Prelog Priority Rules. The compounds of this disclosure may also exist as a mixture of "E" and "Z" isomers. Substituents around a cycloalkyl or heterocycloalkyl are designated as being of cis or trans configuration. Furthermore, the disclosure contemplates the various isomers and mixtures thereof resulting from the disposal of substituents around an adamantane ring system. Two substituents around a single ring within an adamantane ring system are designated as being of Z or E relative configuration. For examples, see C. D. Jones, M. Kaselj, R. N. Salvatore, W. J. le Noble J. Org. Chem. 1998, 63, 2758-2760 and E. L. Eliel, and S. H. Wilen. (1994) Stereochemistry of Organic Compounds. New York, N.Y.: John Wiley & Sons, Inc.

The compounds may also contain asymmetrically substituted carbon atoms in the R or S configuration, in which the terms "R" and "S" are as defined by the IUPAC 1974 Recommendations for Section E, Fundamental Stereochemistry, Pure Appl. Chem. (1976) 45, 13-10. Compounds having asymmetrically substituted carbon atoms with equal amounts of R and S configurations are racemic at those carbon atoms. Atoms with an excess of one configuration over the other are assigned the configuration present in the higher amount, such an excess of about 85%-90%, an excess of about 95%-99%, or an excess greater than about 99%. Accordingly, this disclosure includes racemic mixtures, relative and absolute stereoisomers, and mixtures of relative and absolute stereoisomers.

The compounds used in the methods of the current disclosure containing NH, C(O)OH, OH or SH moieties may have attached thereto prodrug-forming moieties. The prodrug-forming moieties are removed by metabolic processes and release the compounds having the freed hydroxyl, amino or carboxylic acid in vivo. Prodrugs are useful for adjusting such pharmacokinetic properties of the compounds as solubility and/or hydrophobicity, absorption in the gastrointestinal tract, bioavailability, tissue penetration, and rate of clearance.

The compounds used in the various embodiments can also exist in isotope-labeled or isotope-enriched form containing one or more atoms having an atomic mass or mass number different from the atomic mass or mass number most abundantly found in nature. Isotopes can be radioactive or non-radioactive isotopes. Isotopes of atoms such as hydrogen, carbon, phosphorous, sulfur, fluorine, chlorine, and iodine include, but are not limited to, $^{2}H$, $^{3}H$, $^{13}C$, $^{14}C$, $^{15}N$, $^{18}O$, $^{32}P$, $^{35}S$, $^{18}F$, $^{36}Cl$, and $^{125}I$. Compounds that contain other isotopes of these and/or other atoms are within the scope of this disclosure.

In another embodiment, the isotope-labeled compounds contain deuterium ($^{2}H$), tritium ($^{3}H$) or $^{14}C$ isotopes. Isotope-labeled compounds of this disclosure can be prepared by the general methods well known to persons having ordinary skill in the art. Such isotope-labeled compounds can be conveniently prepared by carrying out the procedures disclosed in the Examples disclosed herein and Schemes by substituting a readily available isotope-labeled reagent for a non-labeled reagent. In some instances, compounds may be treated with isotope-labeled reagents to exchange a normal atom with its isotope, for example, hydrogen for deuterium can be exchanged by the action of a deuteric acid such as $D_2SO_4/D_2O$. In addition to the above, relevant procedures and intermediates are disclosed, for instance, in Lizondo, J et al., Drugs Fut, 21(11), 1116 (1996); Brickner, S J et al., J Med Chem, 39(3), 673 (1996); Mallesham, B et al., Org Lett, 5(7), 963 (2003); PCT publications WO1997010223, WO2005099353, WO1995007271, WO2006008754; U.S. Pat. Nos. 7,538,189; 7,534,814; 7,531,685; 7,528,131; 7,521,421; 7,514,068; 7,511,013; and US Patent Application Publication Nos. 20090137457; 20090131485; 20090131363; 20090118238; 20090111840; 20090105338; 20090105307; 20090105147; 20090093422; 20090088416; and 20090082471, the methods are hereby incorporated by reference.

The isotope-labeled compounds of the disclosure may be used as standards to determine the effectiveness of Bcl-2 inhibitors in binding assays. Isotope containing compounds have been used in pharmaceutical research to investigate the in vivo metabolic fate of the compounds by evaluation of the mechanism of action and metabolic pathway of the nonisotope-labeled parent compound (Blake et al. J. Pharm. Sci. 64, 3, 367-391 (1975)). Such metabolic studies are important in the design of safe, effective therapeutic drugs, either because the in vivo active compound administered to the patient or because the metabolites produced from the parent compound prove to be toxic or carcinogenic (Foster et al., Advances in Drug Research Vol. 14, pp. 2-36, Academic press, London, 1985; Kato et al., J. Labelled Comp. Radiopharmaceut., 36(10):927-932 (1995); Kushner et al., Can. J. Physiol. Pharmacol., 77, 79-88 (1999)).

In addition, non-radioactive isotope containing drugs, such as deuterated drugs called "heavy drugs," can be used for the treatment of diseases and conditions related to Bcl-2 activity. Increasing the amount of an isotope present in a compound above its natural abundance is called enrichment. Examples of the amount of enrichment include from about 0.5, 1, 2, 3, 4, 5, 6, 7, 8, 9, 10, 12, 16, 21, 25, 29, 33, 37, 42, 46, 50, 54, 58, 63, 67, 71, 75, 79, 84, 88, 92, 96, to about 100 mol %. Replacement of up to about 15% of normal atom with a heavy isotope has been effected and maintained for a period of days to weeks in mammals, including rodents and dogs, with minimal observed adverse effects (Czajka D M and Finkel A J, Ann. N.Y. Acad. Sci. 1960 84: 770; Thomson J F, Ann. New York Acad. Sci 1960 84: 736; Czakj a D M et al., Am. J. Physiol. 1961 201: 357). Acute replacement of as high as 15%-23% in human fluids with deuterium was found not to cause toxicity (Blagojevic N et al. in "Dosimetry & Treatment Planning for Neutron Capture Therapy", Zamenhof R, Solares G and Harling O Eds. 1994. Advanced Medical Publishing, Madison Wis. pp. 125-134; Diabetes Metab. 23: 251 (1997)).

Stable isotope labeling of a drug can alter its physicochemical properties such as pKa and lipid solubility. These effects and alterations can affect the pharmacodynamic response of the drug molecule if the isotopic substitution affects a region involved in a ligand-receptor interaction. While some of the physical properties of a stable isotope-labeled molecule are different from those of the unlabeled one, the chemical and biological properties are the same, with one important exception: because of the increased mass of the heavy isotope, any bond involving the heavy isotope and another atom will be stronger than the same bond between the light isotope and that atom. Accordingly, the incorporation of an isotope at a site of metabolism or enzymatic transformation will slow said reactions potentially altering the pharmacokinetic profile or efficacy relative to the non-isotopic compound.

The current methods may also incorporate a prodrug form of the selective a compound disclosed herein. Prodrugs are derivatives of an active drug designed to ameliorate some identified, undesirable physical or biological property. The physical properties are usually solubility (too much or not enough lipid or aqueous solubility) or stability related, while problematic biological properties include too rapid metabolism or poor bioavailability which itself may be related to a physicochemical property. Prodrugs are usually prepared by: a) formation of ester, hemi esters, carbonate esters, nitrate esters, amides, hydroxamic acids, carbamates, imines, Mannich bases, phosphates, phosphate esters, and enamines of the active drug, b) functionalizing the drug with azo, glycoside, peptide, and ether functional groups, c) use of aminals, hemi-aminals, polymers, salts, complexes, phosphoramides, acetals, hemiacetals, and ketal forms of the drug. For example, see Andrejus Korolkovas's, "Essentials of Medicinal Chemistry", John Wiley-Interscience Publications, John Wiley and Sons, New York (1988), pp. 97-118, which is incorporated in its entirety by reference herein.

Furthermore, the methods of the current disclosure may involve administration of the compounds having The formula by, for example, at least one mode selected from parenteral, subcutaneous, intramuscular, intravenous, intraarticular, intrabronchial, intraabdominal, intracapsular, intracartilaginous, intracavitary, intracelial, intracerebellar, intracerebroventricular, intracolic, intracervical, intragastric, intrahepatic, intramyocardial, intraosteal, intrapelvic, intrapericardiac, intraperitoneal, intrapleural, intraprostatic, intrapulmonary, intrarectal, intrarenal, intraretinal, intraspinal, intrasynovial, intrathoracic, intrauterine, intravesical, bolus, vaginal, rectal, buccal, sublingual, intranasal, and transdermal.

As previously stated, the "therapeutically effective amount" of the current disclosure refers to that amount of the compound being administered sufficient to prevent development of or alleviate to some extent one or more of the symptoms of the condition or disorder being treated. Therapeutically effective amounts of compounds having the formula depend on the recipient of the treatment, the disorder being treated and the severity thereof, the composition containing the compound, the time of administration, the route of administration, the duration of treatment, the compound potency, its rate of clearance and whether or not another drug is co-administered. Generally, the methods of the current disclosure involve administering a dose of the selective Bcl-2 inhibitor ranging from about 0.001 mg/kg to about 1000 mg/kg. In one embodiment, the methods involve administering a dose of selective Bcl-2 inhibitor ranging from about 0.01 mg/kg to about 500 mg/kg. In a further embodiment, the methods involve administering a dose of selective Bcl-2 inhibitor ranging from about 0.1 mg/kg to about 300 mg/kg.

EXAMPLES

Reduced SDH Activity in ABT-199 Sensitive MM

Figure 1B:
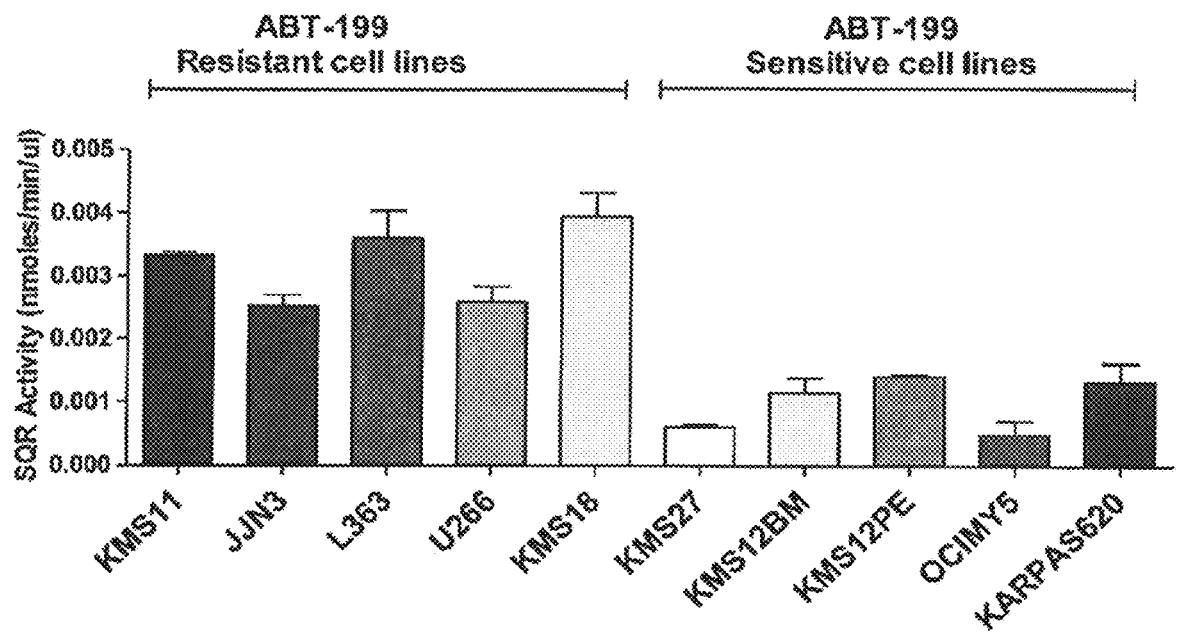
FIG. 1B shows data indicating succinate ubiquinone reductase activity correlates with ABT-199 sensitivity in myeloma cell lines. Evaluation of SQR activity in ABT-199 sensitive and resistant myeloma cell lines correlated with decrease in absorbance of DCIP (Results are representative of 4 independent evaluations with the mean and SEM plotted in calculation of SQR activity in nmoles/min/µl demonstrating lower SQR activity in sensitive cells.

SDH/respiratory Complex II is an enzyme that has a direct role both in the TCA cycle and electron transport chain and consequently OCR and oxidative phosphorylation. Complex II activity was evaluated in ABT-199 sensitive and resistant cells. SDH consists of 4 subunits: SDHA (FAD binding site), SDHB (Fe—S containing subunit), SDHC and SDHD (containing a heme band ubiquinone binding Qp site). Electrons released from SDHA upon the oxidation of succinate to fumarate are transferred sequentially from FAD to Fe—S clusters to ubiquinone at the Qp site. The reduction of ubiquinone bound in the Qp site to ubiquinol is referred to as the ubiquinone reductase activity of SDH. The reduction of ubiquinone facilitates the extrusion of protons from Complex III facilitating ATP synthesis. SQR activity is measured in live permeabilized cells, with intact mitochondria by pre-treating with inhibitors of Complex I (rotenone) and Complex III (antimycin) leaving Complex II/SDH activity intact. SQR activity correlates with electron transfer from ubiquinone bound in SQR's Qp site to the redox sensitive dye, DCIPIP. The assay is validated by detection of SDH activity only upon addition of the substrate succinate and lack of activity upon addition of malonate (SDHA inhibitor) or SQR inhibitor thenoyltrifluoroacetone (TTFA) (FIG. 1A). ABT-199 sensitive cells exhibit low SQR activity while resistant lines including t(11;

14) U266 exhibit high SQR activity (FIG. 1), importantly correlating with ABT-199 sensitivity.

Inhibition of SQR with Qp Site Inhibitor Thenoyltrifluoroacetone (TTFA) Sensitizes Resistant Cells to ABT-199

Figure 2A:
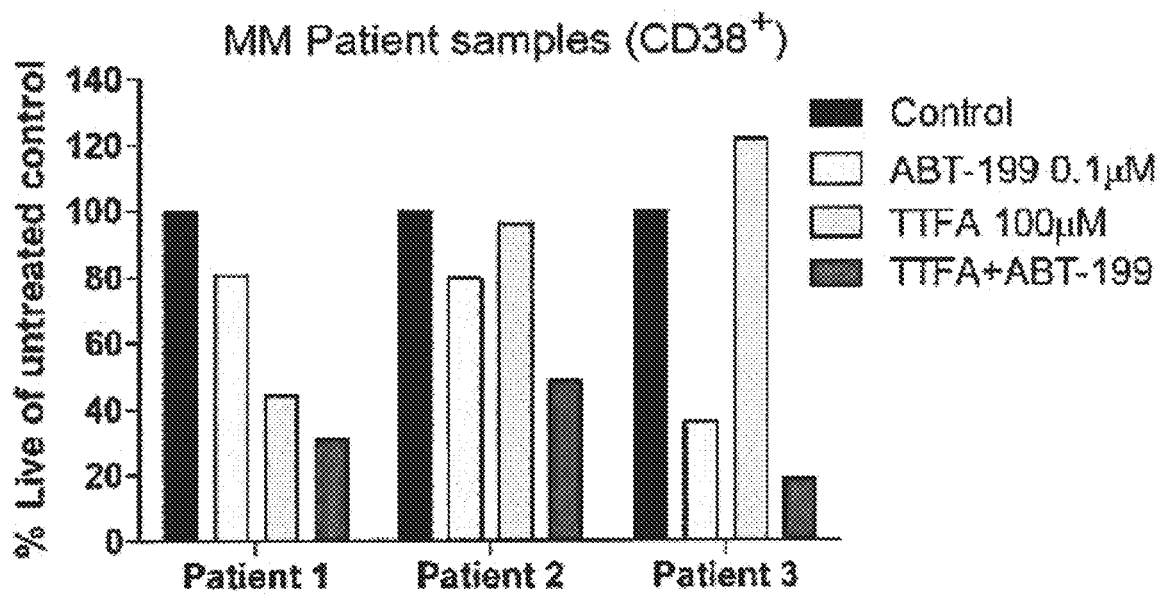
FIG. 2A shows data indicating inhibition of Complex II/SQR by TTFA sensitizes MM lines and patient cells to ABT-199. CD38+ve MM cells from myeloma patient samples exhibit significant cytotoxicity upon combinatorial treatment with TTFA (100 µM) and ABT-199 (0.5 µM) for 48 hrs. Complex I inhibition with piercidin or SDHA inhibition with 3-NPA. L363, MM.15 and KMS 11 cells were cultured in the presence or absence of 0.S µM ABT-199 with or without either Complex I inhibitor piericidin (0.001 mM) or Complex II inhibitor 3NPA (1 mM) or TTFA (100 µM) for 24 hrs. SQR activity evaluated in Patient #3 is low and comparable to other sensitive lines.
Figure 2B:
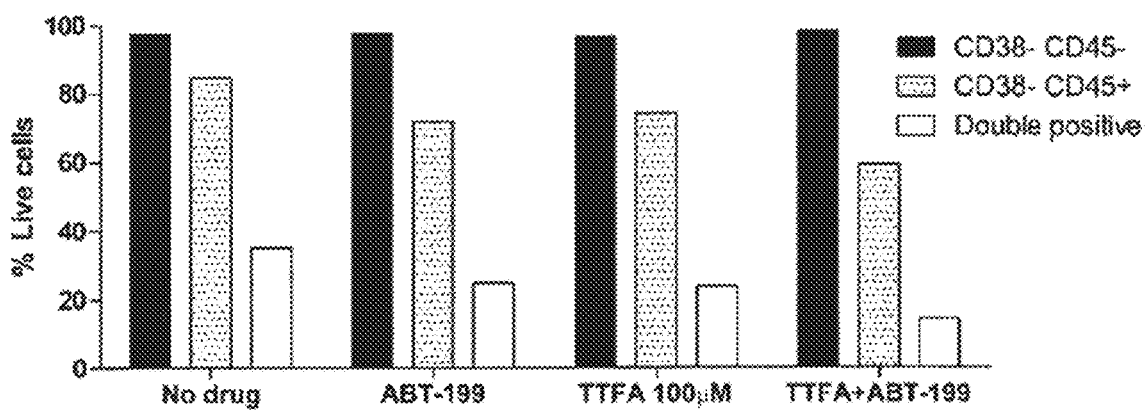
FIG. 2B shows data indicating normal cell populations contained within the bone marrow aspirate of patient sample #2 did not exhibit significant cytotoxicity with either ABT-199/TTFA or the combination. Synthetic lethality are not cytotoxic as a single agent in cell lines or primary normal cells associated with a myeloma patient sample. In sum, these results indicate SQR regulates Bcl-2 dependence and ABT-199 sensitivity and validate that SQR activity is predictive of ABT-199 sensitivity and response in MM.
Figure 3:
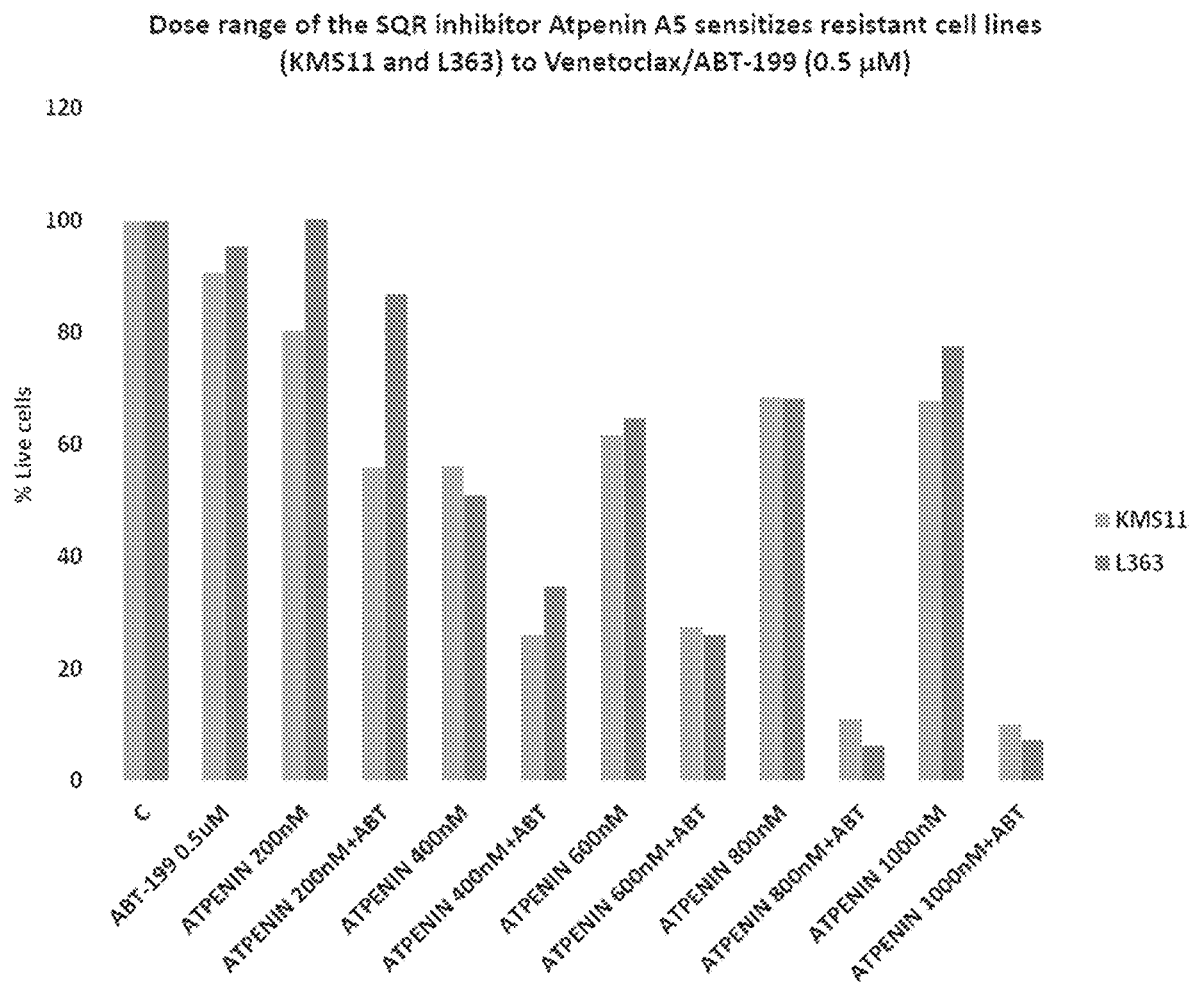
FIG. 3 shows data indicating the Complex II inhibitor atpenin A5 sensitizes resistant cell lines.
Figure 4:
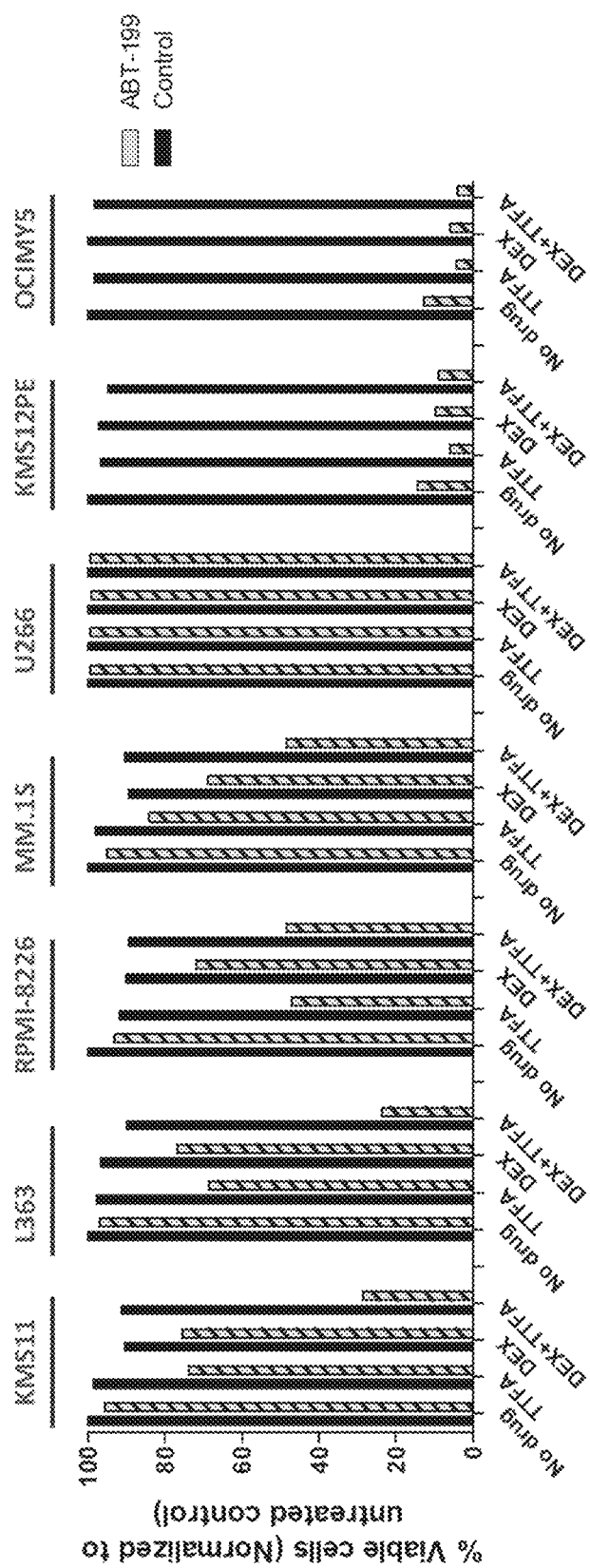
FIG. 4 shows data Complex II inhibitor with TTFA sensitizes MM cells to ABT-199 and is additive to Dex-induced death. KMS11, L363, RPMI-8226, MM.1S, U266 (ABT-199 resistant cell lines) and KMS12PE and OCIMY5 (ABT-199 sensitive cell lines) were cultured in presence of SQR inhibitor TTFA (100 uM) or DEX (0.5 uM) either alone or in combination with ABT-199 (0.5 uM) for 24 hrs. Cell viability was assessed by Annexin V-DAPI staining and Flow cytometry.
Figure 5A:
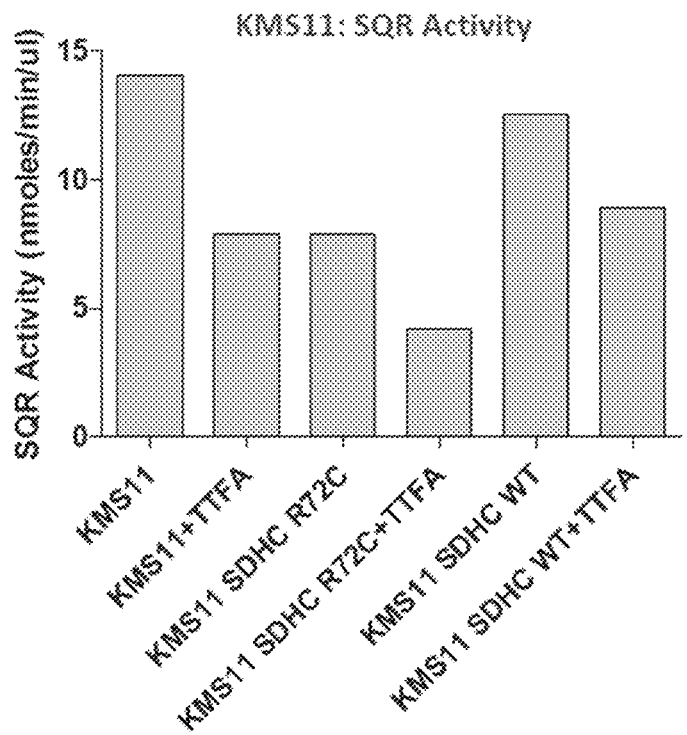
FIG. 5A shows data indicating mutation at Qp site in SDHC inhibits SQR activity and sensitizes KMS11 to ABT-199. KMS 11 cells exhibiting SDHCKO and overexpressing SDHCWT or SDHCR72C mutant cDNA, were cultured in presence of SQR inhibitor TTFA (100 uM) for 24 hrs. Succinate Ubiquinone Reductase activity was assessed as a function of DCPIP absorbance at 600 nm.
Figure 5B:
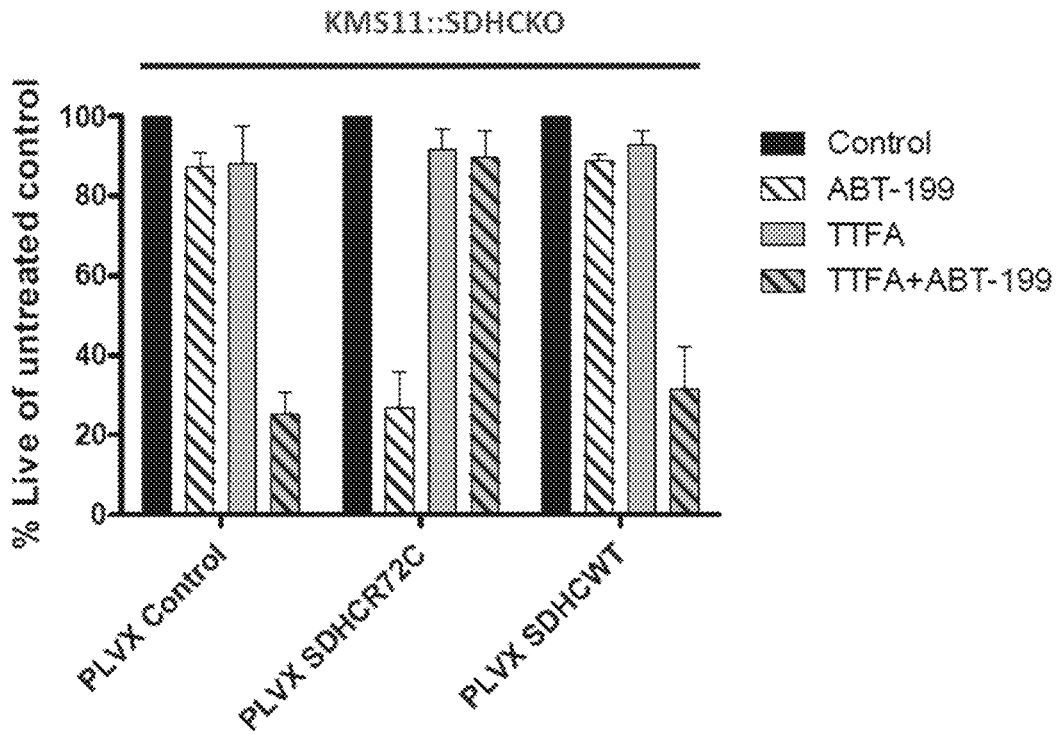
FIG. 5B shows data on cells from FIG. 5A that were also treated or not treated with ABT-199 (0.5 uM) for 24 hrs. Cell viability was assessed by Annexin V-DAPI staining and Flow cytometry.

Reduced SQR activity in ABT-199 sensitive cells prompted testing to determine whether inhibition of SQR with the Qp site inhibitor TTFA sensitizes resistant MM to ABT-199. The maximal dose of TTFA that did not cause cytotoxicity in MM was tested. This amount inhibited SQR activity. Resistant MM lines were treated with TTFA and/or a dose range of ABT-199 and cell death evaluated by Annexin V/DAPI staining. Inhibition of SQR induced potent sensitization to ABT-199 in resistant lines and MM patient cells (FIG. 2A). Importantly, patient sample #3 was a t(11;14) ABT-199 sensitive sample that had low SQR activity confirming our hypothesis that reduced SQR activity correlates with ABT-199 sensitivity. Inhibition of Complex I or Complex III with 3NPA (which targets the SOHA subunit) at the maximum dose that did not elicit cytotoxicity, were not as effective as TTFA in inducing sensitization to ABT-19 underscoring the importance of targeting the Qp site for effective sensitization to ABT-199. TTFA or ABT-199 individually did not elicit cytotoxicity in MM. Importantly; normal cells contained within a myeloma patient sample did not exhibit significant cytotoxicity upon treatment with TTFA and ABT-199 (FIG. 2B) supporting selective cytotoxicity in tumor cells.

The invention claimed is:

1. A method of comprising,
   a) isolating a sample of cancer cells from a subject,
   b) mixing the sample with mitochondrial complex II, succinate, and ubiquinone; and
   c) measuring succinate ubiquinone reductase (SQR) activity providing measured SQR activity and diagnosing the subject as sensitive to or in need of a chemotherapy treatment comprising administering a Bcl-2 inhibitor, if the measured SQR activity is lower than a control level.

2. The method of claim 1, wherein the Bcl-2 inhibitor is venetoclax.

3. The method of claim 2, further comprising the step of recording the measurements.

4. The method of claim 3, wherein the measurements are recorded in an electronic format.

5. The method of claim 1, further comprising the step of recording the diagnosis.

6. The method of claim 5, wherein the diagnosis is recorded in an electronic format.

7. The method of claim 6, further comprising the step of reporting the measurements or diagnosis to a medical professional, the subject, or representative thereof.

8. The method of claim 1, further comprising administering an effective amount of Bcl-2 inhibitor in combination with a mitochondrial complex II inhibitor to the subject.

9. A method of diagnosing and treating multiple myeloma comprising,
   a) isolating a sample of myeloma cells from a subject,
   b) mixing the sample with mitochondrial complex II, succinate, and ubiquinone; and
   c) measuring succinate ubiquinone reductase (SQR) activity providing measured SQR activity; and
   d) treating the subject with venetoclax if the measured SQR activity is lower than a control level.

* * * * *